(12) United States Patent
Yang et al.

(10) Patent No.: US 11,813,123 B2
(45) Date of Patent: Nov. 14, 2023

(54) ULTRASOUND RESPONSIVE MICRO-COMPOSITE MARKERS

(71) Applicant: The Regents of the University of California, Oakland, CA (US)

(72) Inventors: Jian Yang, San Diego, CA (US); Alexander Liberman, San Diego, CA (US); James Wang, San Diego, CA (US); Christopher Barback, San Diego, CA (US); Natalie Mendez, La Jolla, CA (US); Erin Ward, La Jolla, CA (US); Sarah Blair, La Jolla, CA (US); Andrew C. Kummel, San Diego, CA (US); Tsai-Wen Sung, Fremont, CA (US); William C. Trogler, Del Mar, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 650 days.

(21) Appl. No.: 16/329,669

(22) PCT Filed: Aug. 31, 2017

(86) PCT No.: PCT/US2017/049714
§ 371 (c)(1),
(2) Date: Feb. 28, 2019

(87) PCT Pub. No.: WO2018/045222
PCT Pub. Date: Mar. 8, 2018

(65) Prior Publication Data
US 2019/0192253 A1 Jun. 27, 2019

Related U.S. Application Data
(60) Provisional application No. 62/381,739, filed on Aug. 31, 2016.

(51) Int. Cl.
*A61B 90/00* (2016.01)
*A61B 8/08* (2006.01)
(Continued)

(52) U.S. Cl.
CPC ............ *A61B 90/39* (2016.02); *A61B 8/0841* (2013.01); *A61B 8/12* (2013.01); *A61B 8/14* (2013.01);
(Continued)

(58) Field of Classification Search
CPC .. A61K 49/223; A61K 49/225; A61K 31/729; A61K 51/048; A61B 90/39;
(Continued)

(56) References Cited

U.S. PATENT DOCUMENTS 6,749,554 B1 * 6/2004 Snow .................... A61L 29/085
600/3
2005/0123482 A1 6/2005 Unger
(Continued)

FOREIGN PATENT DOCUMENTS

WO WO-2014052911 A * 4/2014 ........... A61K 49/223

OTHER PUBLICATIONS

Zou et al., Preparation of silica-based surface-imprinted core-shell nanoadsorbents for the selective recognition of sulfamethazine via reverse atom transfer radical precipitation polymerization, J Polym Res (2014) 21:520, DOI 10.1007/s10965-014-0520-6 (Year: 2014).*
Bedasso et al., Boron-based nanostructures: Synthesis, functionalization, and characterization, ProQuest Dissertations And Theses ; Thesis (Ph.D.)—Northern Illinois University, 2015.; Publication No. AAT 10008888; ISBN: 9781339455921; Source: Dissertation Abstracts International, vol. 77-06(E) (Year: 2015).*
(Continued)

*Primary Examiner* — John Denny Li
(74) *Attorney, Agent, or Firm* — PERKINS COIE LLP

(57) ABSTRACT

Ultrasound imaging is a non-invasive, non-radioactive, and low cost technology for diagnosis and identification of implantable medical devices in real time. Developing new ultrasound activated coatings is important to broaden the utility of in vivo marking by ultrasound imaging. Ultrasound
(Continued)

responsive macro-phase segregated micro-composite thin films were developed to be coated on medical devices composed of multiple materials and with multiple shapes and varying surface area. The macro-phase segregated in films having silica micro-shells in polycyanoacrylate produces strong color Doppler signals with the use of a standard clinical ultrasound transducer. Electron microscopy showed a macro-phase separation during slow curing of the cyanoacrylate adhesive, as air-filled silica micro-shells were driven to the surface of the film. The air sealed in the hollow space of the silica shells acted as an ultrasound contrast agent and echo decorrelation of air exposed to ultrasound waves produces color Doppler signals.

20 Claims, 24 Drawing Sheets

(51) Int. Cl.
| | | |
|---|---|---|
| *A61K 49/22* | (2006.01) | |
| *A61K 31/729* | (2006.01) | |
| *A61K 51/04* | (2006.01) | |
| *A61B 8/12* | (2006.01) | |
| *A61B 8/14* | (2006.01) | |

(52) U.S. Cl.
CPC ............ *A61B 8/481* (2013.01); *A61K 31/729* (2013.01); *A61K 49/223* (2013.01); *A61K 51/048* (2013.01); *A61B 2090/3929* (2016.02); *A61B 2562/0204* (2013.01); *A61B 2562/12* (2013.01)

(58) Field of Classification Search
CPC ........... A61B 8/0841; A61B 8/12; A61B 8/14; A61B 8/481; A61B 2090/3929; A61B 2562/0204; A61B 2562/12
See application file for complete search history.

(56) References Cited

U.S. PATENT DOCUMENTS

| | | | |
|---|---|---|---|
| 2009/0297441 A1* | 12/2009 | Canham | A61K 49/0047 424/1.61 |
| 2013/0034609 A1* | 2/2013 | Liu | C08F 292/00 428/404 |
| 2015/0165072 A1* | 6/2015 | Assouline | A61M 5/007 600/409 |
| 2015/0273061 A1 | 10/2015 | Trogler et al. | |
| 2017/0027660 A1* | 2/2017 | Blair | A61B 8/481 |
| 2018/0344641 A1* | 12/2018 | Brinker | A61K 9/127 |

OTHER PUBLICATIONS

Chen et al., Synthesis and antioxidant activity of phosphorylated polysaccharide from Portulaca oleracea L. with H3PW12040 immobilized on polyamine functionalized polystyrene bead as catalyst, Journal of Molecular Catalysis A: Chemical 342-343 (2011) 74-82, doi:10.1016/j.molcata .2011.04.014 (Year: 2011).*
Sinopharm Chemical Reagent Co. Ltd (Shanghai, China)—Diethylenetriamine (Year: 2022).*
Chu, "Hydrogel superglue is 90 percent water" Nov. 9, 2015. MIT News Office. Retrieved from http://news.mit.edu/2015/hydrogel-superglue-water-adhesive-1109 on Oct. 20, 2017. 1 page.
DOW "Ethyleneamines" Aug. 2001. Retrieved from heep://www.dow.com/amines/pdfs/108-01347.pdf on Oct. 20, 2017. 3 pages.
ISA, International Search Report and Written Opinion for International Application No. PCT/US17/49714. dated Nov. 17, 2017. 9 pages.
ISA, International Preliminary Reporton Patentability for International Application No. PCT/US17/49714. dated Mar. 14, 2019. 8 pages.
Njdhss, "Methyl 2-Cyanoacrylate" Feb. 2000. Retrieved from http://nj.gov/health/eoh/rtkweb/documents/fs/1241 .pdf on Oct. 20, 2017. 1 page.
Yang, et al. "Ultrasound Responsive Macrophase-Segregated Microcomposite Films for in Vivo Biosensing" ACS Applied Materials & Interfaces, 2017, 9, pp. 1719-1727.

* cited by examiner

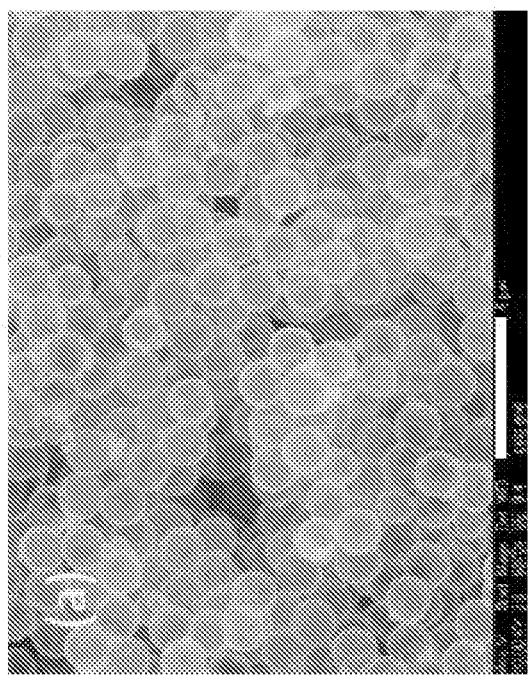
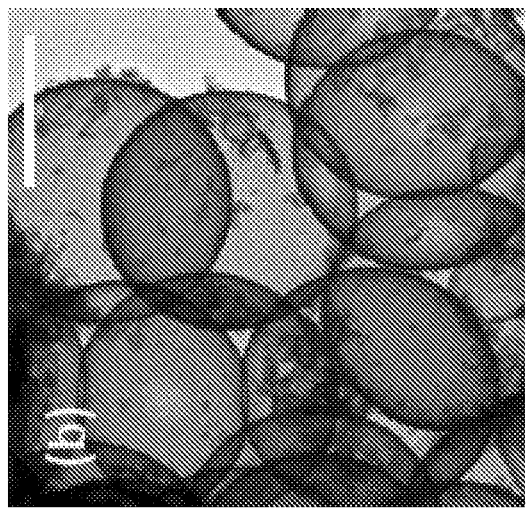
FIG. 10(a)
FIG. 10(b)

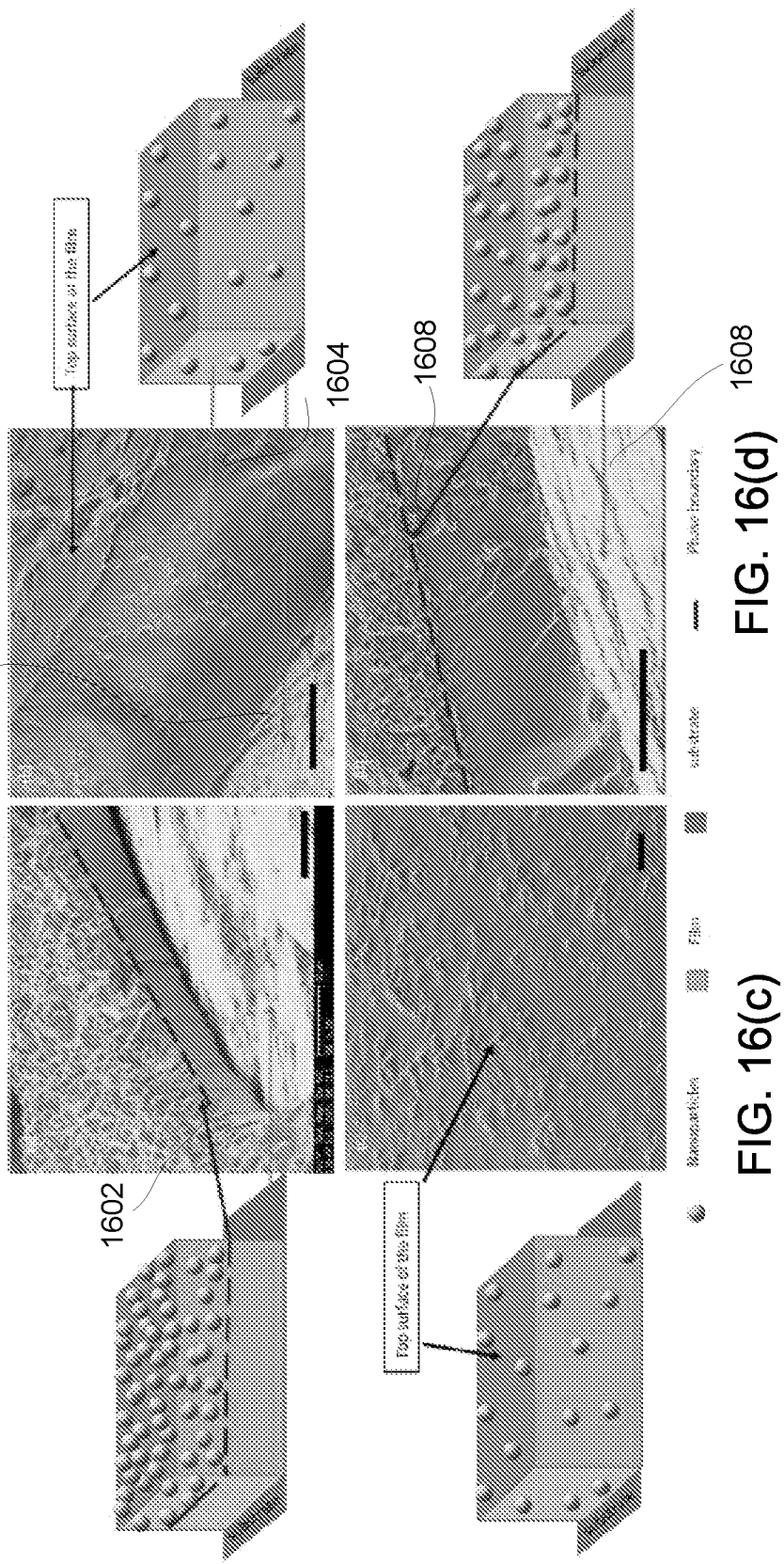

US 11,813,123 B2

ULTRASOUND RESPONSIVE MICRO-COMPOSITE MARKERS

STATEMENT OF RELATED APPLICATIONS

This application is a 371 National Phase Application of PCT Application No. PCT/US2017/049714 entitled "ULTRASOUND RESPONSIVE MICRO-COMPOSITE MARKERS", filed on Aug. 31, 2017, which claims the benefit of U.S. Provisional Patent Application No. 62/381,729 entitled "ULTRASOUND RESPONSIVE MICRO-COMPOSITE MARKERS FOR IN VIVO BIO-SENSING", filed on Aug. 31, 2016. The entire contents of the aforementioned patent applications are incorporated by reference herein.

TECHNICAL FIELD

This patent document relates to systems, devices, and processes that are related to ultrasound activated markers for medical devices.

BACKGROUND

Medical ultrasound imaging, also known as diagnostic sonography or ultrasonography, is a diagnostic imaging technique based on the application of ultrasound. It is used to examine internal body structures, such as tendons, muscles, joints, vessels and internal organs, to find a source of a disease or to exclude any pathology. Compared to other modalities of medical imaging, ultrasound can provide real-time images, and is portable and low in cost.

Furthermore, it does not present the risk of harmful ionizing radiation.

SUMMARY OF CERTAIN EMBODIMENTS

Techniques, systems, and devices are disclosed that relate to ultrasound activated markers and associated fabrication techniques to provide ultrasound responsive properties to medical devices for effective in vivo detection.

In one exemplary aspect, an ultrasound activated marker is disclosed. The ultrasound activated marker comprises a layer of polymeric matrix; and hollow shells at least partially embedded in the layer of polymeric matrix and positioned close to a top surface of the layer of polymeric matrix, wherein each of the hollow shells is configured to retain air in a hollow core to provide an ultrasound contrast agent for ultrasound imaging.

In another exemplary aspect, an ultrasound activated marker is disclosed. The ultrasound activated marker comprises a volume of polymeric matrix; and hollow shells, uniformly dispersed in the volume of polymeric matrix, wherein each of the hollow shells is configured to retain air in a hollow core to provide an ultrasound contrast agent for ultrasound imaging.

In another aspect, a method of synthesizing micro-shells used in an ultrasound activated marker is disclosed. The method comprises mixing template beads with a base solution and an organic compound to create a first mixture, wherein the base solution reacts with the organic compound; adding a chemical compound to the first mixture to create a second mixture; adding an organoboron compound to the second mixture to form particles from the template beads; washing and drying the particles; and calcining the particles at a first temperature to obtain micro-shells.

In another exemplary aspect, a method of synthesizing an ultrasound activated device is disclosed. The method includes combining hollow shells with a base solution and a glue to create a mixture; dipping a part of a device into the mixture in multiple cycles to coat the part of the device with multiple layers comprising the mixture, wherein each of the multiple cycles is separated by a time interval; and curing the part of the device to produce an ultrasound activated device.

In yet another exemplary aspect, a medical device is disclosed. The device includes a body; and an ultrasound activated marker coated on at least a part of the body, wherein the ultrasound activated marker includes: a layer of polymeric matrix; and hollow shells at least partially embedded in the layer of polymeric matrix and positioned close to a top surface of the layer of polymeric matrix, wherein each of the hollow shells is configured to retain air in a hollow core to provide an ultrasound contrast agent for ultrasound imaging during medical procedures.

BRIEF DESCRIPTION OF THE DRAWINGS

FIG. 10(a) shows an exemplary SEM image of calcined 2 um boron doped silica micro-shells with scale bars being 5 um.

FIG. 10(b) shows an exemplary transmission electron microscopy (TEM) image of calcined 2 um boron doped silica micro-shells with scale bars being 1 um.

FIG. 16(a) shows an exemplary SEM image of the cross section of the DCM based macro-phase separated film exfoliated from a glass slide.

FIG. 16(b) shows an exemplary SEM image of the cross section of the acetonitrile based film coated on a surgical needle.

FIG. 16(c) shows an exemplary SEM image of the front surface of the film on the surgical needle with acetonitrile as solvent.

FIG. 16(d) shows an exemplary SEM image of the cross section of the acetonitrile based film on a surgical needle (cured in glove box).

DETAILED DESCRIPTION

Figure 1:
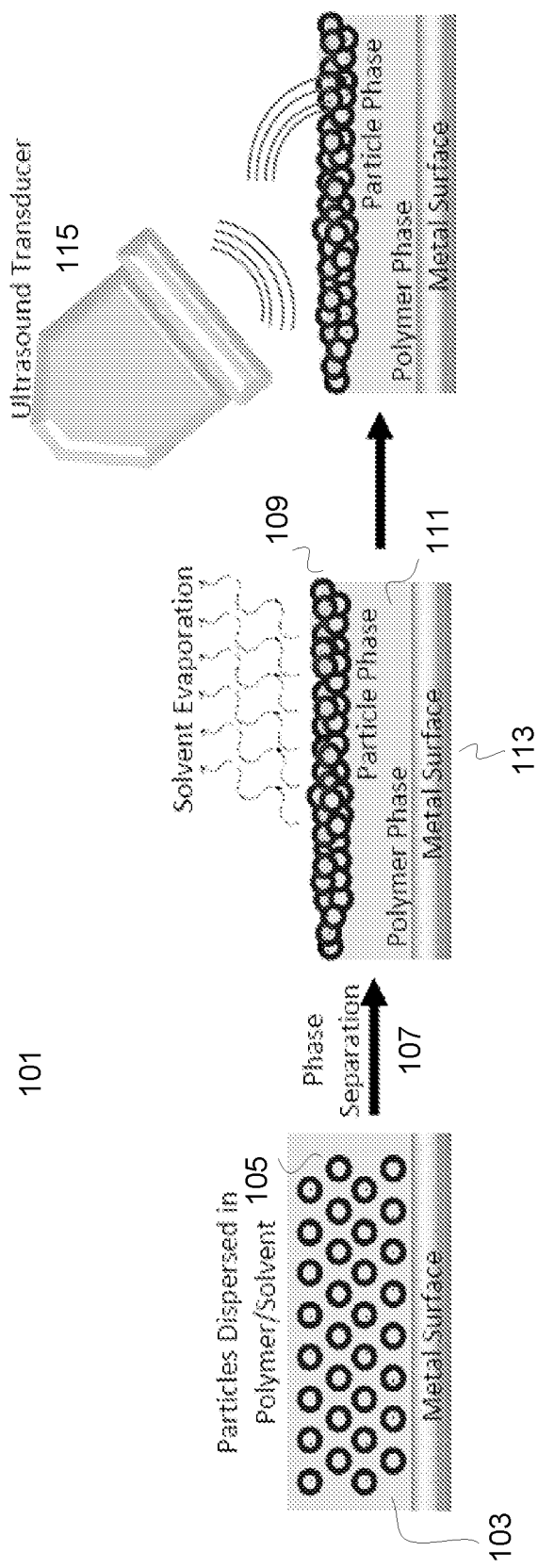
FIG. 1 shows an exemplary scheme of macro-phase separation of PMCA/micro-shells composite during curing.

In this patent document, the word "exemplary" is used to mean serving as an example, instance, or illustration. Any embodiment or design described herein as "exemplary" is not necessarily to be construed as preferred or advantageous over other embodiments or designs. Rather, use of the word exemplary is intended to present concepts in a concrete manner.

Biomedical devices such as needles, catheters, biopsy markers, and guidewires are used widely in the health care field. Biomedical devices are often composed of materials such as stainless steel, titanium, silicon, and polymers. These devices may be implanted within complex physiological environments such as the abdominal cavity, gastrointestinal lumen, or the cardiovascular system. Physicians rely on medical imaging modalities, such as ultrasound, X-ray, or CT scans, to monitor or detect implanted biomedical tools during and after a procedure. Many procedures require precision. For example, to successfully achieve a nerve block, a physician must accurately inject local anesthesia to the target nerve bundles while avoiding surrounding blood vessels and other tissue structures. To minimize the chance of unintentionally damaging surrounding nerves, blood vessels, and tissues while achieving the goal of attaining a nerve block, the needle entry and path through the tissue must be precise. Successful injection of the target area greatly depends on the experience of the medical professional.

Detection of retained surgical items (RSI) in the operating room is another challenge for biomedical imaging technology. Small surgical items such as surgical needles, forceps, sutures, and blades can be accidentally left in patients' bodies after an operation. This may cause adverse consequences such as organ damage, bowel perforation, severe pain, sepsis, and even death. It has been estimated that up to 2000 cases of RSI occur in United States each year. A routine surgical tool count is the most commonly used method to prevent RSI from occurring. Radio frequency (RF) tags attached to large surgical items, such as sponges and gauges, can be detected by a RF reader and help avoid RSI. Nevertheless, a RF tag cannot be attached to small surgical items such as needles. X-ray imaging has been a commonly used method to detect metal in tissues; however, an X-ray technician must be present during surgery and a radiologist is required to review the film. X-ray imaging has been used to identify lost surgical needles and it was found that needles less than 20 mm in length were difficult to identify. Additionally, X-ray imaging exposes the patient and medical personnel to radiation and requires the patient to remain under anesthesia while the X-ray is completed and read by a radiologist. Currently, there is no viable universal platform for real-time detection of various RSIs of different sizes and materials during a surgical operation.

In order to improve injection accuracy of biomedical devices, ultrasound (US) guided needle injection technology was developed and is now widely used in a variety of medical and surgical procedures. Ultrasound guidance is used for needle biopsies and epidurals, and to allow physicians to safely place central venous and arterial catheters. Similarly, because ultrasound imaging is a safe, low cost, and in situ method for detecting in vivo medical devices, new ultrasound biopsy markers can be used to overcome the problem imposed by the use of non-biodegradable material (e.g. metal) and X-ray, which exposes patients to radiation hazard.

While conventional B-mode ultrasound imaging helps visualize a needle during its approach toward the target tissue, B-mode ultrasound has multiple limitations. For instance, B-mode ultrasound exhibits interfering signals due to scattering from various tissues or implants. In light of such limitations, it may be beneficial to develop an ultrasound based platform based on high contrast ultrasound imaging modes, such as color Doppler or contrast-enhanced ultrasound, and apply it to positioning and monitoring implantable biomedical devices.

This patent document discloses a novel technology that includes fabricating an ultrasound activated marker comprising a mixture of a polymeric matrix and organic or inorganic sub-micrometer sized hollow shells. The marker can be activated by clinical ultrasound equipment to give a strong color Doppler signal in human tissues or between human organs.

Examples of applications of this ultrasound active marker include detecting a coated surgical equipment, such as surgical needles, forceps, and razor blades retained in patients' body in operation room, and an injectable polymer gel based biopsy marker. Other examples of applications of this marker include placement of needles and catheters for critical injections (e.g., nerve blocks, central lines, biopsies, injections) that use ultrasound guidance. For injections and the placement of catheters deep within the body using minimally invasive methods, it is often difficult to accurately visualize the tip of the needle or catheter. However, it is important to be able to do this in order to avoid accidental damage to nerves, critical vessels, and other organs, as well as to provide the best therapeutic result. The ultrasound active marker can be used to coat needles or catheters, as well as selectively coat only the tip, in order to improve the accuracy of ultrasound guided placement. The ultrasound active marker can also be used to enhance visibility of nonmetallic catheters and other plastic objects, which offer weak contrast in ultrasound imaging. The new marker differs from some old techniques in being thinner, less than 10 microns. This is useful in retaining the sharpness of the needles.

In some embodiments, a ultrasound active marker is fabricated with 2D or 3D formation to provide an enhanced contrast for ultrasound detection in vivo. The marker includes a polymeric matrix and organic or inorganic hollow shells which are biocompatible and may be made biodegradable. The polymeric matrix provides a scaffold for the hollow shells. The polymers used as matrix can be polymeric adhesives such as epoxy adhesive or cyanoacrylate glue; the polymer can also be polymeric gels such as hydrogels or organogels. The polymeric matrix may cross-link hollow shells. The polymeric matrix can be in a 2D formation as a thin film with a thickness ranging from 15 μm to 100 μm. The film can be coated on the surface of metal, plastic or glass. The matrix can also be in a 3D formation with variable shape and volume that can be directly injected into human tissue.

In some embodiments, the hollow shells have a diameter between 0.1 μm and 10 μm. The hollow shells retain air in the hollow core and act as an ultrasound contrast agent. The matrix with hollow shells can be activated by widely used clinical ultrasound equipment with a transducer frequency between 3 and 15 MHz, thereby providing a strong color Doppler signal for easy identification. The ultrasound active thin film can be coated on surgical equipment, artificial tissues and other implants made with metal, plastic or glass. The detection of 2D and 3D ultrasound activated marker can be carried out during surgery with a portable clinical ultrasound machine without the need to move the patient on the surgical table as required for other imaging modalities such as x-ray, computerized tomography (CT), or magnetic resonance imaging (MRI). The ultrasound imaging produces minimal hazard to the patient and personnel. This technology can detect coated surgical needles as small as 10 mm or injectable ultrasound markers with volumes as small as 50 μl in tissues and organs. In some embodiments, the ultrasound signal can persist as long as 2 hours in vivo. This technique provides a simple and low cost method to detect objects in patients' bodies such as retained surgical items and biopsy markers.

In some embodiments, calcined porous silica nano- and micro-shells with a sol-gel reaction can be synthesized using polystyrene beads as templates and tetramethylorthosilicate (TMOS) as the silica precursor. We have employed this technique to synthesize exemplary 500 nm iron-doped silica shells and 2 μm boron-doped silica shells encapsulating perfluoropentane (PFP) as ultrasound contrast agents for an in vivo stationary tumor marker. Ultrasound tests showed that PFP filled silica nanoshells have superior performance to soft microbubbles for imaging longevity (several weeks) by color Doppler imaging.

In some embodiments, 2 μm boron doped silica hollow shells are synthesized by a sol-gel reaction with polystyrene beads as templates, but the synthesis method can be modified to for multiple sized silica shells with a range of diameters, such as in the range 0.1 μm to 6 μm. Methyl 2-cyanoacrylate can be used as polymeric adhesive to cross-link silica shells to form a thin 2D film that can be coated on metal or glass. The thickness of the methyl 2-cyanoacrylate thin film comprising silica shells can be modified by controlling dip coating parameters and the cyanoacrylate viscosity with solvents. Other types of polymeric matrices can be employed to fabricate thin ultrasound active films. For example, glass slides and surgical needles coated by the silica shell films can be used to test the ultrasound signals. Agarose hydrogel comprising octyl modified 2 μm boron-doped silica particles can be used as an injectable 3D ultrasound marker.

In some embodiments, poly(methyl-2-cyanoacrylate) (PMCA) thin films comprising 2 μm boron-doped silica shells are fabricated. Commercial ultrasound sound imaging systems depict simple differences in acoustic index in B-mode, but they have additional nonlinear imaging modes such as contrast pulse sequencing (CPS) and color Doppler. In color Doppler, only reflected signals shifted in frequency from the incident ultrasound frequency are detected; this signal is sensitive to motion in tissue such as blood flow and expanding gas. When filled with gas, the shells can be activated by widely used clinical ultrasound equipment to exhibit strong color Doppler signals. When the 2 μm particles are fractured during cavitation, the resulting increase in isotropic velocities and pressure results in detected Doppler frequency shifts in all directions. Because of the shell fragmentation, a mosaic Doppler signal is generated. The mosaic signal pattern reflects a fluid with a heterogeneous mixture of sound sources moving in different directions, due to different subpopulations of 2 μm particles being fragmented.

These ultrasound active films can be used to coat a variety of surgical tools. Synthetic cyanoacrylates have been traditionally used as biodegradable tissue adhesives for efficient wound closure or sealing vascular sutures. Initiated by surface hydroxyl groups, cyanoacrylate monomers undergo anionic polymerization rapidly in air at room temperature and the polymerization is catalyzed by moisture. Furthermore, cyanoacrylate polymers have low toxicity and a low rate of infection. Fast-curing poly(methyl-2-cyanoacrylate) can bind to a variety of materials such as metal, plastic, and glass. Polymerization of cyanoacrylate films can be used to encapsulate silica micro-shells while sealing air within the hollow space for ultrasound active coating properties.

FIG. 1 illustrates an exemplary scheme of macro-phase separation 101 of PMCA/micro-shells composite during curing. Cyanoacrylate monomer comprising solvent 103 and porous silica micro-shells 105 are coated on glass slides and surgical needles by dip coating to provide ultrasound active thin films. Umbilical tapes and surgical clips can also be coated with PMCA/micro-shells films for in vivo ultrasound testing. After curing, thin PMCA films were formed with a thickness ranging from 5 μm to 100 μm. The thickness can be controlled by the coating method. The PMCA film encapsulates the micro-shells while simultaneously adhering the composite material to the surface of glass slides or needles. The polymerization of methyl-2-cyanoacrylate monomer was initiated by the adsorbed water or the hydroxyl groups on the surface of silica. In vitro and in vivo ultrasound tests showed that the PMCA/micro-shells films produced a strong color Doppler signal with a good persistence (>6 hours), as required for potential applications to in vivo surgical tool detection. The strong color Doppler signal is associated with a macro-phase separation 107 during film curing to form a surface layer consisting primarily of embedded micro-shells 109 with cyanoacrylate acting as an adhesive matrix; however, the base of the film consists primarily of cyanoacrylate polymer 111 tightly bound to the glass or metal substrate 113. Air filled silica shells were driven to the surface of the polymer matrix and covered by a thin polymer film to trap air in the shells when a solvent was added to slow the rate of curing. This made the film imagable by ultrasound 115. Polarity differences between the polymer/solvent phase and the dispersed silica phase causes segregation of the silica shells to the surface layer during film polymerization and solvent evaporation at room temperature.

EXEMPLARY MATERIALS AND METHODS

Example Materials

In some embodiments, the following materials are used for the fabrication of the micro-composite films. Tetramethylorthosilicate (TMOS), N1-(3-trimethoxysilylpropyl)-diethylenetriamine (DETA), and trimethyl borate (TMB) can be purchased from Sigma-Aldrich (St. Louis, Mo.). 2 μm Polystyrene beads can be purchased from Polysciences (Warrington, Pa.). Loctite® 430™ Super Bonder® Instant Adhesive can be purchased from Henkel Corporation (Rocky Hill, Conn.). 031 Hard stainless steel wires (305 mm length) can be supplied by RF Surgical System, Inc. The wires are cut into short sections with a length of 2 cm and bent into curves to simulate surgical needles. Surgical needles (⅜, taper point, 20 gauge) for the in vivo test can be purchased from Santa Cruz Biotechnology, Inc (Dallas, Tex.). 1½ 20 Gauge hypodermic needles can be purchased from BD Medical (Franklin Lakes, N.J.). Umbilical tape (⅛, cut into sections with length of 15 centimeters) can be purchased from Jorgensen Laboratories Inc (Loveland, Colo.). Titanium surgical clips can be purchased from Teleflex Medical (Research Triangle Park, N.C.).

Example Silica Micro-Shells Synthesis

Figure 2:
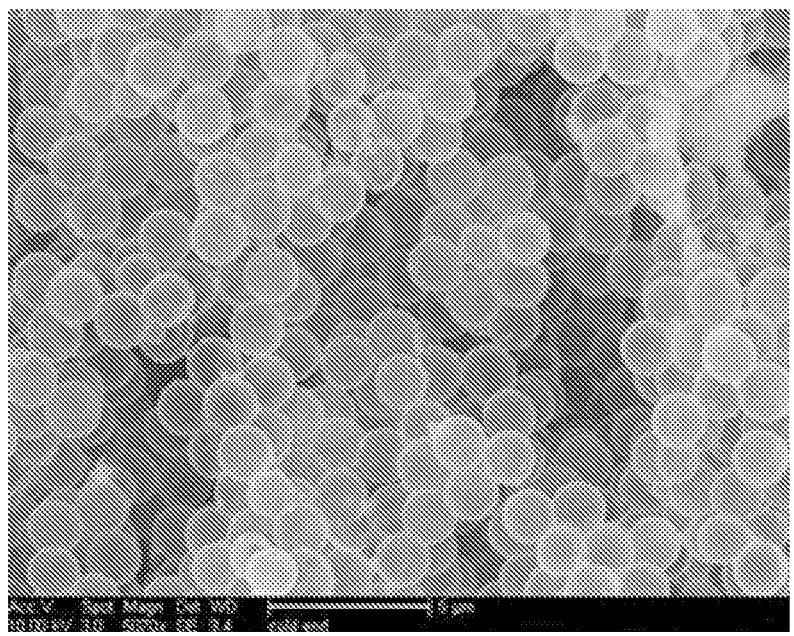
FIG. 2 shows an exemplary scan electron microscopy (SEM) image of hollow silica shells.

The 2 μm calcined boron-doped silica micro-shells can be synthesized by modifying existing methods to improve templating by adding DETA. In one particular example, 100 ml of 95% ethanol was added into a 500 ml cylindrical flask with a magnetic stir bar. 5 ml of 2.6% 2.0 μm polystyrene beads were added to the flask. The mixture was stirred at 1200 rpm at room temperature, while 8 ml of 0.2% DETA in ethanol were added to the flask. DETA adsorbs onto the surface of the polystyrene beads due to electrostatic attraction and provides additional electrostatic attraction for other negatively charged silica precursors, such as hydrolyzed TMOS. The mixture was stirred for 1 hour before 310 μl of TMOS was added. TMOS makes up the majority of the silica micro-shells composition. After about 2 hours, 15 μl of TMB was added and the stirring continued for 5 more hours. TMB can be added to increase the structural integrity of the silica micro-shells. The core-shell particles were then centrifuged and washed with 95% ethanol and re-suspended and washed two more times before drying in air overnight. The dried particles were calcined at 550° C. for 18 hours and produced 17.5 mg of 2 μm micro-shells. A scanning electron microscopy (SEM) image, as shown in FIG. 2, illustrates that the hollow silica shells have a diameter of 1.7-1.8 μm.

In some embodiments, the same synthesis method is employed to make silica hollow shells with diameters of 0.2, 1, 3, and 6 μm using different sized polystyrene beads as templates. In some embodiments, ultrasound active silica hollow shells can be made biodegradable by doping with iron(III) if this is necessary. In some embodiments, hollow shells based on other materials, such as polymers, lipids, or metal oxides comprising air or other gas, can act as silica hollow shells.

In one particular example, octyl modified 2 μm boron-doped silica shells can be fabricated as follows: 10 mg of 2 μm boron doped silica hollow shells are suspended in 2 ml of dimethyl sulfonate. 4 μl of octyltriethoxysilane is added into the mixture and vortexed for 2 hours at room temperature. The modified hollow shells were centrifuged and washed with ethanol before dried in vacuum at 40° C. for 24 hours.

Example Fabrication of Silica Particle Comprising PMCA Films

In one particular example, 10 mg of 2 μm silica micro-shells are suspended in 1.0 ml of dichloromethane (DCM) by sonication and vortex mixed to disperse them before 0.5 ml of methyl-2-cyanoacrylate glue is added. The glue/DCM/micro-shells mixture is coated on glass slides (2 cm×0.5 cm) and surgical needles (length: 15 mm, intersection diameter: 790 μm) by dipping the slides or needles into the liquid mixture. Four groups of glass slide samples are prepared with 1, 2, 3, and 4 cycles of dip coating and each group contained 5 samples. The interval between cycles was 10 minutes. Needles were coated with the PMCA/micro-shells film by dipping the needles into the mixture for 8 cycles. The glue film was cured in air at room temperature for 24 hours. The thickness of the films was measured by a micrometer. Before the ultrasound tests, the films on one side of the glass slides were removed to guarantee that sonographic properties recorded are from a single film. In addition to DCM, ethyl acetate and acetonitrile are also used as solvents to study the relationship between ultrasound performance and the dip coating solvent. The method of coating of surgical clips is the same as coating of surgical needles except that the clips were dip-coated for 4 cycles. For the coating of umbilical tapes, in some implementations, 1 ml of DCM comprising 2 mg of 2 µm silica micro-shells can be added into 0.5 ml of methyl-2-cyanoacrylate glue. The end of the umbilical tape can be dipped into the mixture once. The coated section of the umbilical tape may be 1.0 cm long from the end. The glue can be cured 24 hours at room temperature in air.

Figure 3C:
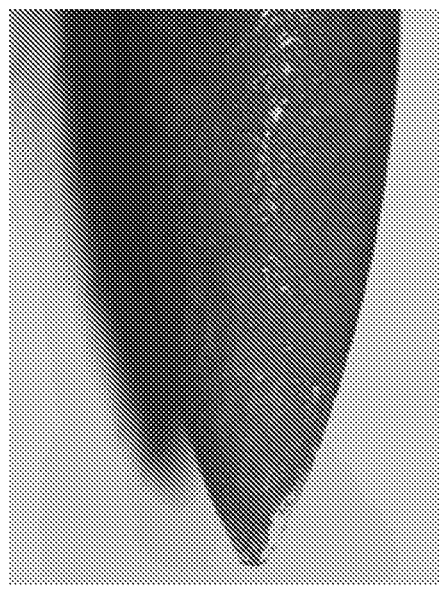
FIG. 3(c) shows an exemplary optical images of methyl 2-cyanoacrylate/2 μm silica hollow shells film coated on the tip of a 20 G injection needle.
Figure 3B:
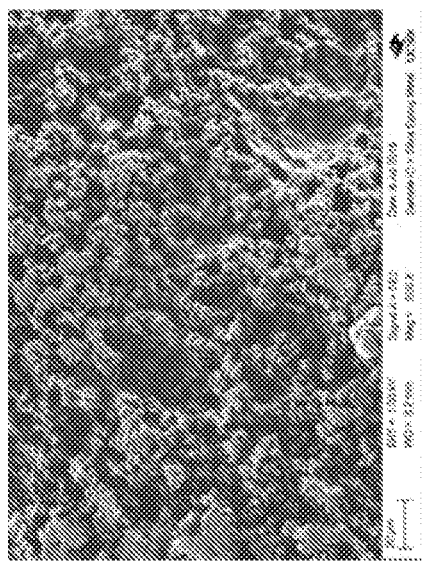
FIG. 3(b) shows an exemplary SEM image cyanoacrylate glue/2 μm boron doped silica hollow shells film on surgical needle.
Figure 3A:
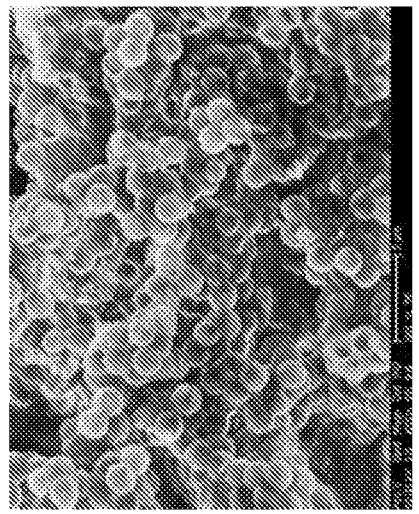
FIG. 3(a) shows an exemplary SEM image of cyanoacrylate glue/2 μm boron doped silica hollow shells film on glass slide.

In some embodiments, the average thickness of glue/particles film on glass slides is 97.6±12.6 um. The average thickness of glue/particles film on needles is 36.4±2.3 um. FIG. 3(a)-(b) show exemplary scanning electron microscopy (SEM) images of cyanoacrylate glue/2 µm boron-doped silica hollow shells film on glass slide (FIGS. 3(a)-3(b)) and surgical needle (FIG. 3(c)). These SEM images show that the particles are bonded by cyanoacrylate glue to form multiple layers of hollow shells with high packing density. The 2-methyl cyanoacrylate monomer polymerizes on the surface of silica shells and forms a thin film. This film blocks the pores of silica and seals air in the hollow space. The air locked in the hollow space is compressed by ultrasound waves and also may be released from the nano-pores in the hollow shells, which gives non-linear ultrasound echo waves. Other polymeric adhesives may act as cyanoacrylate glue and perform the same sonographic properties. In some embodiments, the glue does not fill in the space between the particles but seal the air in the particles. This is achieved for cyanoacrylate by the water in the pores of the particles catalyzing the polymerization and then the excess monomer being readily evaporated. However, ultrasound active films may form with hydrogel which fill in the spaces between the particles. The hydrogel has about the same density as water and behaves as such in ultrasound imaging behavior.

In some embodiments, the coating of particles and cyanoacrylate glue on hypodermic needle tips is synthesized. For example, 10 mg of 2 µm boron-doped silica hollow shells were suspended in 1.0 ml acetonitrile/dichloromethane (1:1) by sonication and vortex. 0.5 ml of methyl 2-cyanoacrylate (lacotite 430) was added. A 20 G hypodermic injection needle tips were dip coated in the mixture for 8 times in 1 hour. The glue film was cured in air at room temperature for 24 hours before imaging. Only the tip of the needle is coated; the length of the film is 0.3 cm from the tip of the needle. A longer coating length can also be applied. The thickness of the films is measured by a micrometer. The thickness of the film on the tip ranges from 5 µm to 10 µm. FIG. 3(c) shows an optical images of the tip of a 20 G injection needle coated by methyl 2-caynoacrylate/2 um silica hollow shells film (the hollow shells cannot be distinctively identified in the figure due to their small sizes).

In some embodiments, a super hydrophilic surface of silica shells/cyanoacrylate glue film can be generated for more effective surface functionalization. For example, diluted silica hollow shells in dichloromethane (DCM)/adhesive mixtures were used as the coating agent. Ozone gas was used to treat the coating and create a hydroxyl and other oxygenated moieties on the surface of the coating. 10 mg of 2 um boron doped silica hollow shells were suspended in 1.0 ml of DCM by sonication and 0.5 ml of methyl 2-cyanoacrylate (Loctite 430) was added; the mixture was then vortexed. The glue/DCM/particles mixture was coated on surgical needles (⅜, 20 gauge) and hypodermic needles (1½, gauge 21) by dipping needles into the liquid mixture 4 times. After the glue films on the substrates were cured at room temperature in air at atmospheric pressure for 24 hours, the substrates were exposed to ultraviolet-generated ozone gas at a flow rate of 1.5-2 L/min for 15-30 minutes. Subsequently, the substrates were covered and stored in a sealed plastic bag. The needles were then soaked in 1% perfluoro-octyl-triethoxysilane in methanol (7.0 mL methanol with 70 uL perfluoro-octyl-triethoxysilane) for 1 hour within 30 minutes of the ozone treatment, before the ozone process to wane. This attaches the perfluoro-octyl-triethoxysilane onto the surface of the needles via active sites generated by ozone processing.

The effect of ozone treatment was assessed by measuring the contact angle of a water droplet on the cyanoacrylate/DCM film before and after the treatment. First, several glass slides were washed with ethanol three times and dried. Then 0.5 ml of DCM and 0.25 ml of methyl 2-cyanoacrylate were vortexed, and 20 µl of the DCM/glue mixture was drop-coated on the surface of each glass slides. The glue films on the slides were cured at room temperature in air at atmospheric pressure for 24 hours. After curing, the glue films were exposed to ultraviolet-generated ozone gas at a flow rate of 2 L/min for 15 minutes. Immediately after the ozone treatment, 10 µL of deionized (DI) water was dropped on both treated and untreated glue films and the contact angles of the water droplets were measured. The treated glue films were then stored in air without cover. After 1 week, 10 µL of DI water was dropped on the aged-treated glue films and the contact angles of the water droplets were measured. The results showed that the average contact angle of water droplets on untreated, treated, and treated-aged glue films were 69.95°, 12.25°, and 38.10°, respectively. The contact angles showed that the ozone treatment dramatically enhanced the hydrophilicity of the surface of the film, and storing the film in air will lead to slow loss of surface hydrophilicity.

Figure 21:
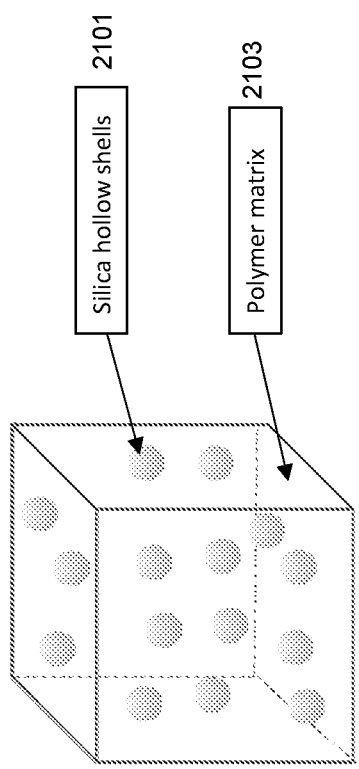
FIG. 21 shows an exemplary scheme of 3D polymer matrix with silica hollow shells.

FIG. 21 shows an exemplary scheme of a 3D marker. The modified silica hollow shells 2101 are uniformly dispersed in the polymer matrix 2103. In some embodiments, 3D ultrasound active marker is 1% agarose hydrogel comprising octyl modified silica hollow shells. The device can be fabricated as follows: 200 mg of agarose is dissolved in 1 ml of distilled water at 70° C. 4 mg of octyl 2 µm silica hollow shells are suspended in 1 ml of distilled water. The hollow shells/water suspension is added into the agarose solution and mixed with vigorous stirring. The mixture was cooled at room temperature until the gelation finished and a firm gel was obtained.

Exemplary Techniques for Optical and Electronic Microscopic Imaging and Contact Angle Measurement Optical microscopy can be used to visualize PMCA/micro-shell films on needles. Transmission electron microscopy (TEM) analysis of boron doped micro-shells has been performed with use of a JEOL (JEOL, Tokyo, Japan) ARM200F operated at 200 kV. TEM samples are prepared by suspending calcined silica micro-shells in ethanol and dropped onto a lacey carbon film grid substrate. Scanning electron microscopy (SEM) images of micro-shells and films can be obtained using a FEI/Philips XL30 FEG ESEM microscope with an accelerating voltage ranging from 1.5 kV to 10 kV. SEM samples are prepared by depositing micro-shells or film coated needles on a carbon tape substrate. Combined field emission SEM (FE-SEM) images can be obtained using a Sigma 500 FE-SEM (Zeiss, Germany) with an accelerating voltage ranging from 0.8 kV to 20 kV. FE-SEM samples are prepared with the same procedure employed for the TEM samples. The contact angles of the films on glass slides are measured by analyzing the photograph of the water drop on the films with ImageJ.

Exemplary In Vitro and In Vivo Ultrasound Testing

In the following examples, in vitro and in vivo ultrasound tests were performed using a Siemens Acuson Sequoia 512 Ultrasound machine with the Acuson 15L8 and 4C1 transducers with center frequencies of 7 MHz and 3 MHz, respectively. Software used for analysis of data included SanteDicom Viewer (Athens, Greece) and Microsoft Excel (Redmond, Wash.). The tests of ultrasound responsive films on glass slides were performed with the samples in a water tank. The 15L8 ultrasound transducer was clamped in the water tank with the sample film facing the transducer. The film was imaged with color Doppler ultrasound with a mechanical index (MI) of 1.9, which is the highest MI permitted by FDA for diagnostic ultrasound imaging. The glass slides were kept in water and subjected to continuous ultrasound radiation for 60 minutes. The color Doppler signals were recorded over several time periods. The attenuating rates of color Doppler signals were studied by measuring the areas of the signals and comparing the areas with that of the initial signals.

Figure 4:
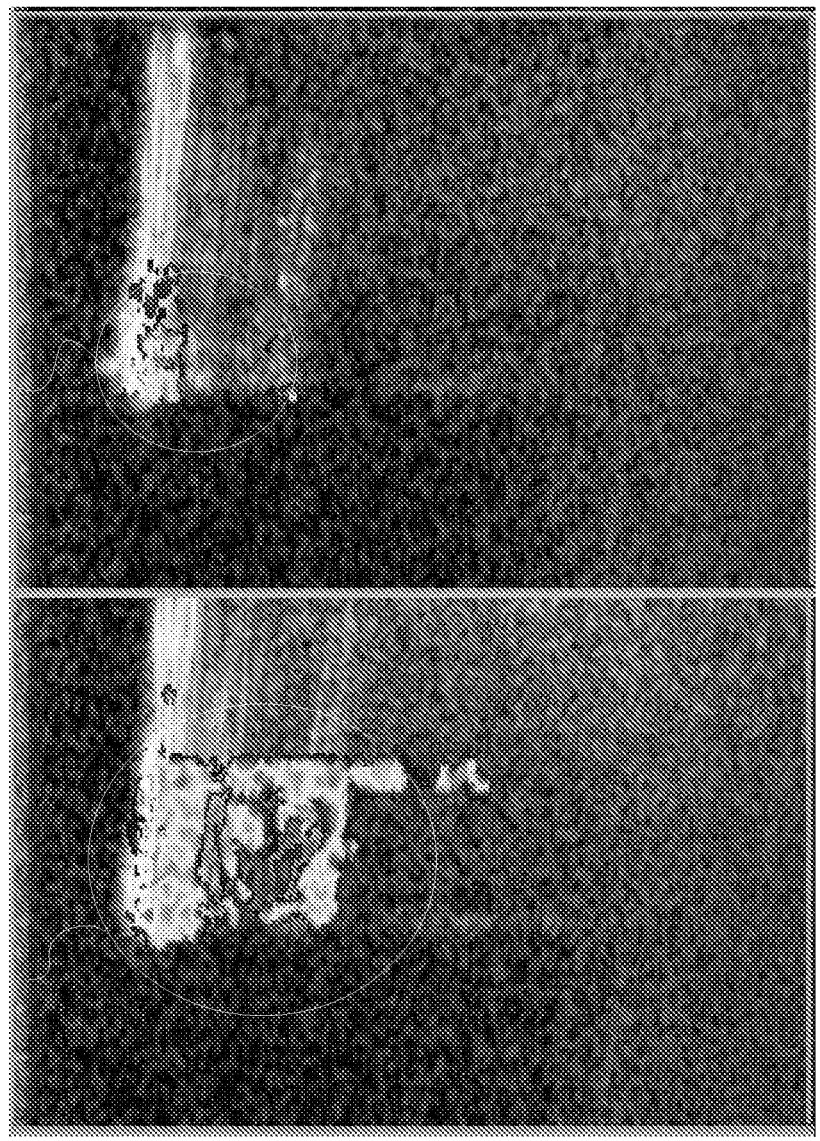
FIG. 4 shows an exemplary ultrasound image (color Doppler mode) of cyanoacrylate glue/2 um hollow silica shells film on glass slide.

FIG. 4 shows the sonographic image (color Doppler mode) of signal of glue/hollow shells film on glass slide. The film gave a strong color Doppler signal 401 at the beginning of the test. The signal 403 was still apparent after the film was subjected to continuous ultrasound waves for 60 minutes. In another test the coated glass slide was dipped in distilled water for 72 hours and then tested with ultrasound. The color Doppler signal was as strong as the freshly coated film on a glass slide. The excellent sonographic properties indicate that the poly(cyanoacrylate) film on the surface of silica shells can seal the pores of silica and keep air within the hollow space, which subsequently works as an ultrasound contrast agent. The polymer film also exhibit good water resistance so the air can be kept within the hollow shell for an extended period of time.

In some implementations, in vitro ultrasound testing of glue/particles film coated needles was performed in a plastic box with a dimension of 20 cm×15 cm×6 cm. The box was filled with raw chicken livers to simulate organs in a surgical field. A PMCA/micro-shells film coated needle was placed in the box. The distance between the needle and the top layer of chicken livers was controlled between 0.5 cm to 6 cm. The ultrasound properties were studied with an ACUSON Sequoia ultrasound system with a 15L8 (central frequency of 7-15 MHz) and a 4C1 transducer (central frequency of 3-5 MHz). In another in vitro test, chicken thigh with skin was used to simulate muscle tissues and coated needles were punctured and stayed in the muscle. The depth of the needles was between 0.5 cm and 3.0 cm from the skin.

Figure 5B:
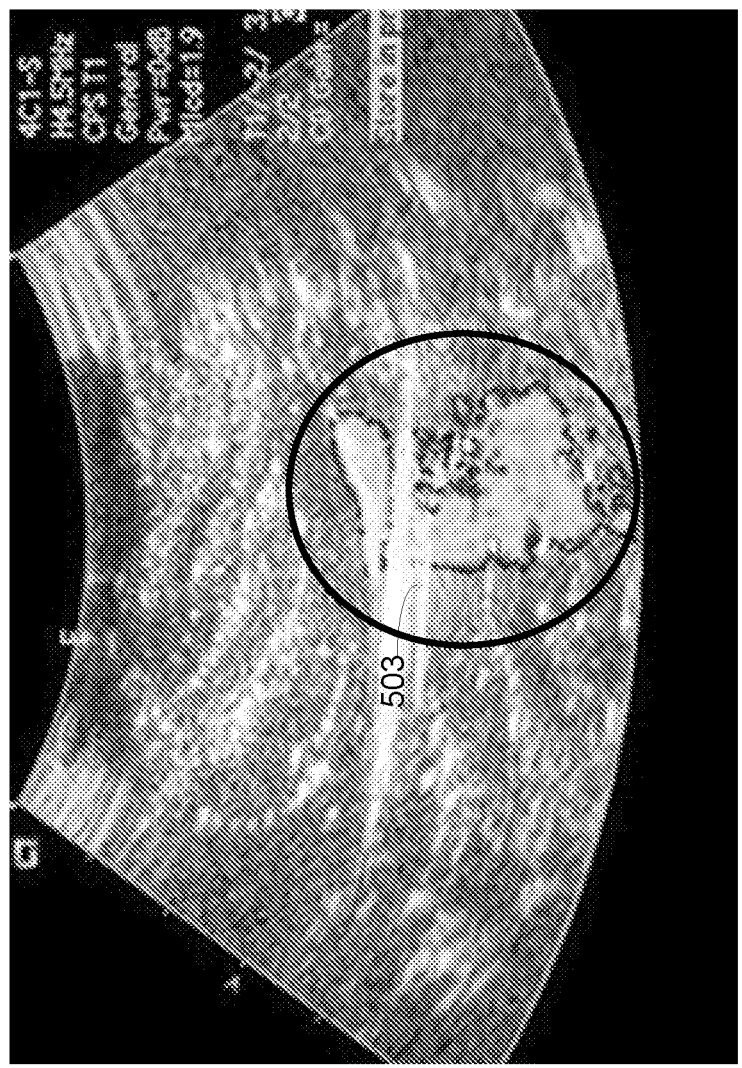
FIG. 5(b) shows an exemplary ultrasound image (color Doppler mode) of cyanoacrylate glue/2 μm hollow silica shells film surgical needle in chicken liver with 4C1 transducer.
Figure 5A:
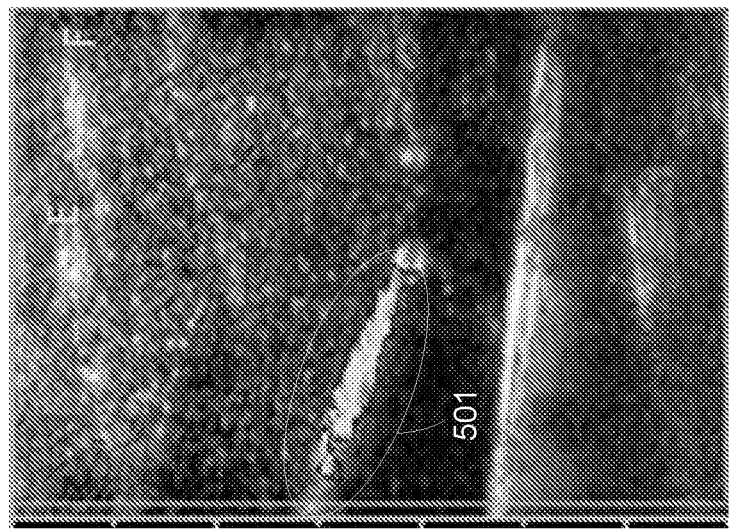
FIG. 5(a) shows an exemplary ultrasound image (color Doppler mode) of cyanoacrylate glue/2 μm hollow silica shells film surgical needle in chicken liver with 15L8 transducer.

FIG. 5(a) and FIG. 5(b) are sonographic images of ultrasound activate film coated needle in chicken livers. FIG. 5(a) shows an exemplary ultrasound image (color Doppler mode) of cyanoacrylate glue/2 µm hollow silica shells film surgical needle in chicken liver with 15L8 transducer. The color Doppler signals distinguish the needle 501 from the grey background of the chicken livers. FIG. 5(b) shows an exemplary ultrasound image (color Doppler mode) of cyanoacrylate glue/2 µm hollow silica shells film surgical needle in chicken liver with 4C1 transducer. The color Doppler signals also distinguish the needle 503 from the grey background of the chicken livers. With the ultrasound images the position and the depth of the film coated needle are easy to fix by the observer for removal.

Figure 6:
FIG. 6 shows an exemplary ultrasound image (color Doppler mode) of cyanoacrylate glue/2 μm hollow silica shells film surgical needle in a chicken leg with 4C1 transducer.
Figure 7:
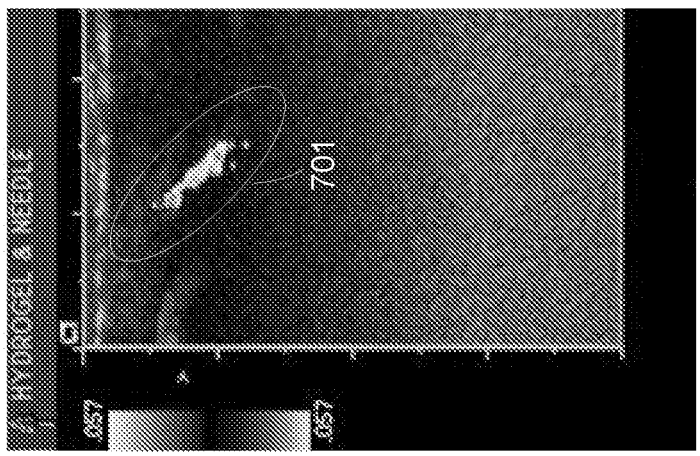
FIG. 7 shows an exemplary ultrasound image (color Doppler mode) of cyanoacrylate glue/2 μm hollow silica shells film surgical needle injected and stayed in a chicken leg with 4C1 transducer.

In another test, a chicken leg was used as a phantom of human tissue for a muscle environment. An ultrasound activate film coated needle was sutured through the chicken leg 30 times before being placed in chicken livers for detection. The color Doppler signals were collected. FIG. 6 shows the color Doppler signals collected of the needle 601 as initially placed in the chicken leg and the needle 603 after 3 hours staying in the chicken leg. FIG. 7 shows the color Doppler signals collected as the needle 701 was punctured and stayed in the chicken leg. In both cases, the color Doppler signal was strong enough to distinguish the needle from the background of the chicken leg by the observer.

Figure 24A:
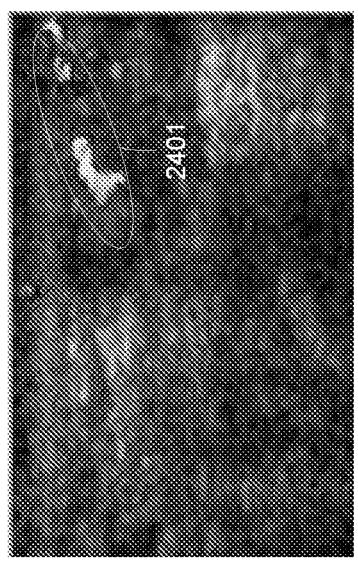
FIG. 24(a) shows exemplary color Doppler signals of unprocessed coated hypodermic needles.
Figure 24B:
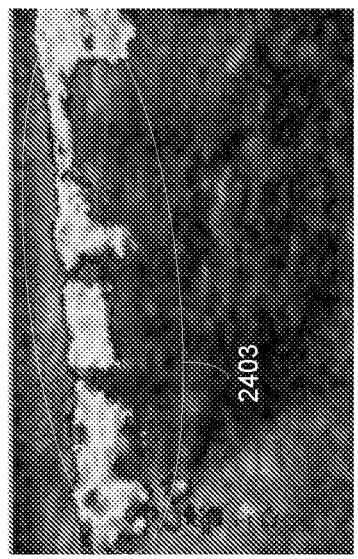
FIG. 24(b) shows exemplary color Doppler signals of processed coated hypodermic needles.

FIG. 24(a) and FIG. 24(b) show color Doppler ultrasonography images of unprocessed coated 2401 and multistage processed coated 2403 21G hypodermic needles, respectively, inside a living rabbit. A 15L8 transducer was used with a frequency of 7 MHz. The coated needles were tested in vivo. The multi-stage processing of needle coating showed a higher initial intensity of ultrasound color Doppler signal and gave consistent results. Furthermore, the fat-resistant coating was more effective than without the ozone pretreatment. Color Doppler signals were obtained from multi-stage processed needles after 10 injections through rabbit's tissues.

Figure 8B:
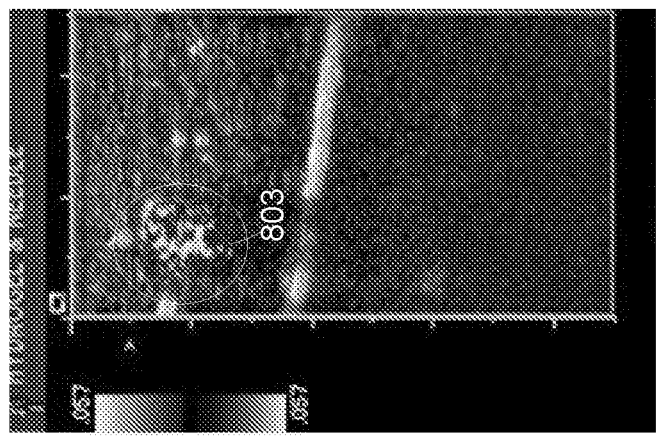
FIG. 8(b) shows an exemplary ultrasound images (color Doppler mode) of 1% agarose hydrogel comprising 2 mg/ml octyl modified silica hollow shells in pork liver with 4C1 transducer.
Figure 8A:
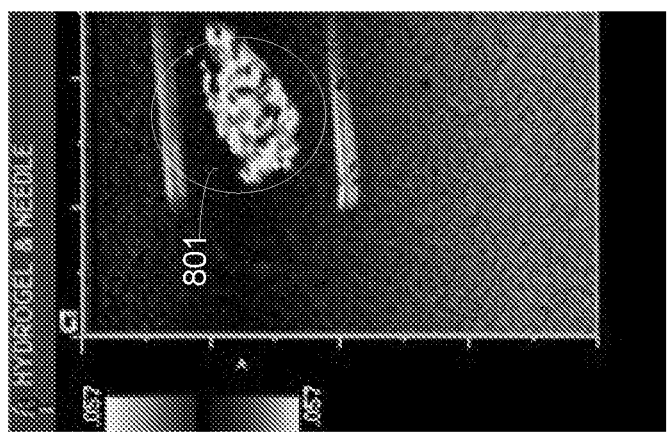
FIG. 8(a) shows an exemplary ultrasound image (color Doppler mode) of 1% agarose hydrogel comprising 2 mg/ml octyl modified silica hollow shells in a plastic pipette.

FIG. 8(a) shows the ultrasound images (color Doppler mode) of 1% agarose hydrogel comprising 2 mg/ml octyl modified silica hollow shells 801 in a plastic pipette. The hydrogel was put into a plastic pipette for the ultrasound test in water tank with a 4C1 transducer. In another test the gel was cooled to 40-45° C. and 50 µl of liquid gel was injected into a pork liver, as shown in FIG. 8(b). After 10 minutes a 4C1 transducer was used to detect the hydrogel 803 in the liver tissues.

Figures 9A, 9B:
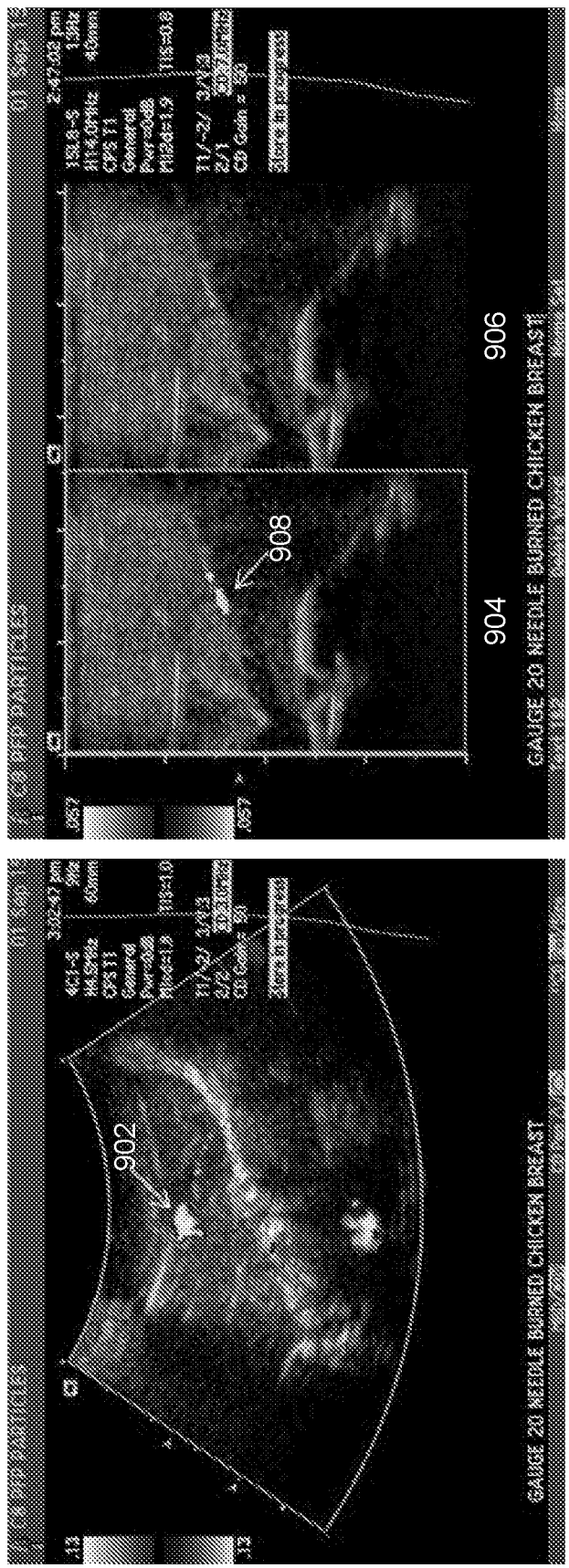
FIG. 9(a) shows an exemplary ultrasound color Doppler image of coated hypodermic injection needle tip in chicken breast.
FIG. 9(b) shows an ultrasound color Doppler and B mode image of coated hypodermic injection needle tip in chicken breast.

Ex vivo ultrasound testing of glue/particles film coated needles was performed using a chicken breast (750 grams) without skin to simulate human tissues. A tip coated 20 G injection needle was stabbed into the chicken breast. The distance between the needle and the surface of the chicken breast was controlled between 0.5 cm to 3 cm deep. The ultrasound properties were studied with an ACUSON Sequoia ultrasound system with a 15L8 transducer (7-15 MHz) and a 4C1 transducer (3-5 mHz). FIG. 9(a) shows an exemplary ultrasound color Doppler image of coated hypodermic injection needle tip in chicken breast with 4C1 transducer. The needle is in profile and only the tip gives color Doppler signal 902. The other color Doppler feature is a shadow which can be removed by using higher frequency ultrasound or lower MI. FIG. 9(b) shows an ultrasound color Doppler 904 and B mode 906 image of coated hypodermic injection needle tip in chicken breast with 15L8 transducer. The needle is in profile and only the tip gives color Doppler signal 908.

In vivo ultrasound testing of PMCA/micro-shell film coated needles, umbilical tapes and surgical clips was performed using female New Zealand white rabbits purchased from Western Oregon Rabbitry and housed individually in a UCSD vivarium facility. They were kept on a 12 hour light/dark cycle and given water and Harlan Teklad commercial pellet diet ad libitum. All animal protocols were approved by the UCSD IACUC.

Rabbits were anesthetized with isoflurane and placed on a warmed water pad. The abdomen was shaved and depilated. Instruments and materials were cleaned and sanitized, but not sterilized. Gel was placed on the tip of the ultrasound transducer.

Once anesthetized, heart rate and SpO2 were monitored via pulse oximetry and jaw tone, mucous membrane color, and pedal reflexes were also observed. A midline incision was made from the xiphoid process to the groin; the abdominal wall was retracted. Sharp dissection was used to enter the peritoneal cavity; subsequently, needles were randomly placed throughout to simulate a clinical situation in which a needle breaks off a suture and needs to be retrieved. The surgeon used a 15L8 transducer to explore and locate the needle and ultrasound signals were recorded. PMCA/micro-shell film coated umbilical tapes and surgical needles were tested with the same method. Once all items were found, imaged and removed, then retraction of the abdomen was ceased and the animal was sacrificed immediately following the surgeon's search.

Same coating method can be used to coat this ultrasound activate film on other metal, plastic, glass, and other surgical items such as forceps and surgical blades. This would help the surgical team detect and locate the positions of any such items left in human body. The imaging can be performed before final closure of the surgical entry wound.

Example Post-Processing Detection of Film Signal

The films were imaged using the color Doppler imaging mode which may display color signals from the film, vascular blood flow, or movement from the transducer or subject. Videos were saved along with simultaneous B-mode and color Doppler images in compressed DICOM format and were post-processed to selectively highlight signal from the film. Signal from the film was distinguishable by its persistent Doppler signal with high spatial and temporal heterogeneity collocated with a strong B-mode signal. Spatial heterogeneity was quantified by calculating the maximum magnitude of the spatial gradient across each of the red, green, and blue (RGB) color channels. Persistence was determined by finding pixels with high spatial heterogeneity lasting at least 3 frames (~0.2 seconds). Temporal heterogeneity for each pixel was calculated by integrating the difference in RGB colors from frame to frame. Pixels matching all criteria were shown using a green color overlay to distinguish from the color Doppler color map. This processed signal (shown in green in the figures) will henceforth be referred to as micro-shell signal (MSS). These methods were developed in MATLAB R2015a (The MathWorks Inc., Natick, Mass.).

Signal properties for detection of the film were compared between imaging in B-mode, color Doppler, and MSS. Color Doppler and MSS have sensitivities of 0.767 and 0.499 and specificities of 0.886. Sixteen video clips from the in vivo experiments of film coated needles were used for analysis. The ultrasound signals were obtained from micro-shells/cyanoacrylate glue film coated stainless steel wires. 4% of the frames were randomly sampled (n=69), and a user defined region-of-interest (ROI) was drawn around needle if present. All pixels outside of the ROI were considered background. B-mode signal-to-noise ratio (SNR) was calculated as the ratio of integrated B-mode image intensity inside the ROI vs. outside. Color Doppler and MSS SNR were calculated as the ratio of the area of detected signal inside the ROI vs outside. Color Doppler and MSS sensitivity was calculated as the area of detected signal inside the ROI divided by the area of the ROI; specificity was calculated as the area of undetected signal outside the ROI divided by the area outside the ROI. As shown in Table 1, Doppler, and processed micro-shells image signal (MSS) have signal to noise ratios (SNRs) of 0.034, 0.061, and 1.639, respectively.

TABLE 1

Cumulative signal properties over all frames.

|  | SNR | Sensitivity | Specificity |
| --- | --- | --- | --- |
| B-mode | 0.0341 | n/a | n/a |
| Doppler | 0.0606 | 0.7668 | 0.8863 |
| MSS | 1.6394 | 0.4993 | 0.9973 |

SNR was also compared between B-mode, Doppler, and MSS using the Kruskal-Wallis test with multiple comparisons. Sensitivity and specificity were compared between Doppler and MSS using the Mann-Whitney U-test. Statistical analyses were performed in MATLAB R2015a (The MathWorks Inc., Natick, Mass.). For the Kruskal-Wallis tests comparing SNRs and Mann-Whitney U-tests comparing sensitivities and specificities, p-value was less than 0.0001 and 0.997 respectively. The Doppler detection has slightly improved SNR over B-mode, but MSS has substantially improved SNR compared to both. Relative to color Doppler, MSS trades a reduction in sensitivity for an increase in specificity. The ultrasound signals were obtained from micro-shells/cyanoacrylate glue film coated stainless steel wires.

The statistics of signal properties measured on a frame-by-frame basis are presented in Table 2 and exhibit similar trends. The median, first quartile (Q1), and third quartile (Q3) of SNR for B-mode, Doppler, and MSS were 0.028 (0.015-0.061), 0.180 (0.072-0.300), and 3.457 (1.372-7.563), respectively. Sensitivities for Doppler and MSS were 0.824 (0.704–0.926) and 0.566 (0.341–0.712), and specificities were 0.957 (0.930–0.980) and 0.999 (0.997–1.000), respectively. SNRs were compared with the Kruskal-Wallis test with multiple comparisons, and sensitivities and specificities were compared with the Mann-Whitney U-test, and all tests showed statistically significant differences ($p<0.0001$).

TABLE 2

Statistics of signal properties measured frame-by-frame.

| Metric | Image | Median | Q1 | Q3 |
| --- | --- | --- | --- | --- |
| SNR | B-mode | 0.0279 | 0.0146 | 0.0614 |
|  | Doppler | 0.1803 | 0.0715 | 0.2996 |
|  | MSS | 3.4572 | 1.3724 | 7.5625 |
| Sensitivity | Doppler | 0.8242 | 0.7037 | 0.9261 |
|  | MSS | 0.5659 | 0.3412 | 0.7122 |
| Specificity | Doppler | 0.9574 | 0.9296 | 0.9799 |
|  | MSS | 0.9994 | 0.9973 | 1.0000 |

Exemplary Synthesis of 2 µm Boron Doped Silica Micro-Shells

FIG. 10(a) and FIG. 10(b) illustrate the TEM and SEM images of boron-doped silica micro-shells. The size and size distribution of the hollow spherical particles were determined from SEM image analysis. The average diameter and standard deviation was 1.71±0.03 um (n=20). The thickness of the silica wall was determined by TEM images analysis was found to be 30±5 nm (n=20). The silica shells have a dense, uniform wall with no resolved pore structure, although the porous shell readily permits gases, solvents, and molecules to diffuse in and out. In TEM images, some colloidal silica particles were observed with a diameter of less than 50 nm attached to the surface of the silica micro-shells.

In some embodiments, non-modified 2 μm beads were employed as templates and boron was doped into the silica matrix during the sol-gel condensation to enhance the mechanical strength of the micro-shells. DETA can be used to serve as both the cationic electrolyte and a precursor of silica to better modify the surface of PS beads. The short, positively charged DETA is absorbed to the surface of anionic zeta potential PS beads, and at the same time the silyl end of DETA was cross linked by the poly-condensation reaction with itself and templated a positively charged surface silica gel network before adding the bulk of TMOS along with trimethyl borate to make the silica shell more robust. Since the hydrolysis and poly-condensation of trimethy borate is faster than TMOS, it may be added 2 hours after TMOS addition. The core-shell sol-gel coated microparticles were obtained by centrifugation, and calcined at 550° C. to remove the PS cores. Dehydration of the sol gel during calcination resulted in a porous hollow silica gel shell with a diameter smaller than the 2 micron template.

Exemplary PMCA/Microshell Films Coated on Glass Slides and Surgical Needles

Figure 11:
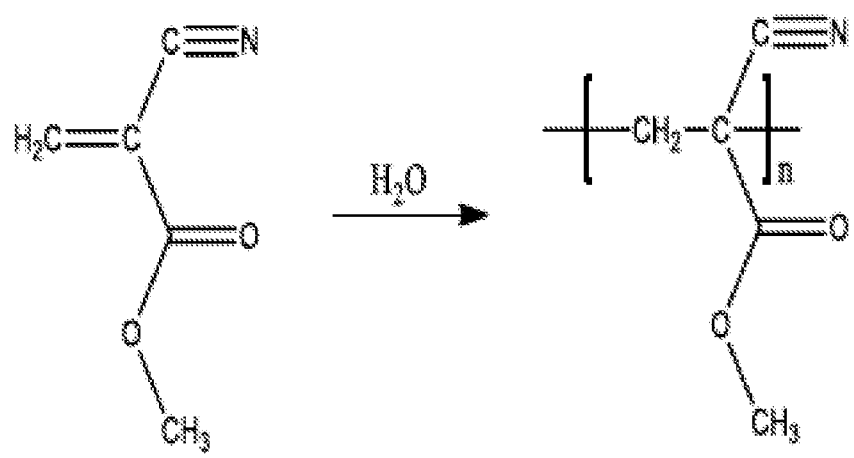
FIG. 11 shows an exemplary polymerization of methyl-2-cyanoacrylate.

Cyanoacrylate glue may be used to cross-link silica micro-shells and bind them as thin films to metal or glass surfaces. In one example, Loctite® 430 was chosen as the cyanoacrylate material because it has low viscosity, which makes it easy to mix with silica shells. The active ingredient is methyl-2-cyanoacrylate which bonds strongly with metal and cures rapidly compared to other synthetic cyanoacrylate adhesives. Organic co-solvents may be used to further disperse silica micro-shells within the glue solution, which lowered the viscosity and slowed curing. The mechanism of the curing of cyanoacrylate glue can be by anionic polymerization of cyanoacrylate monomer. FIG. 11 shows an exemplary polymerization of methyl-2-cyanoacrylate. Cyanoacrylate monomers undergo a rapid anionic polymerization on exposure to basic catalysts such as water. The curing of commercial cyanoacrylate glue is initiated when water, a weak base, neutralizes the strong acid inhibitor added to cyanoacrylate glue. For the PMCA/micro-shells films, the water is likely supplied from the trace amount of water absorbed on the calcined porous silica gel shells.

Some embodiments indicate that water, which initiates the poly-condensation of cyanoacrylate, is already adsorbed on the 2 um silica micro-shells dispersed in acetonitrile before mixing. For example, two sealed tubes that were prepared were identical, except one omitted the silica micro-shells. Both samples were cured at room temperature. The viscosity of the glue mixture comprising silica shells increased rapidly and turned into a white solid within 24 hours. The sample without added silica shells remained liquid for at least 7 days. This indicated that the curing of cyanoacrylate glue was likely initiated by water adsorbed on the surface of the silica shells.

In some embodiments, silica micro-shells were dried in a glovebox for 24 hours at room temperature and then suspended in a glue/acetonitrile solution in a sealed tube. After 24 hours, the viscosity of the suspension increased but did not solidify. The same test was performed without drying the silica shells in the glovebox, and the suspension solidified within 24 h. This shows the water is adsorbed on the silica micro-shells that were not dried. The hydroxyl groups on the silica shells may play a minor role, but the water absorbed on the shells dominates the curing process.

When the acetonitrile solvent was replaced with DCM, the curing time of glue comprising silica micro-shells was prolonged to 3 days in sealed tubes. This can be attributed to the solubility of water in acetonitrile being much higher than in DCM. Acetonitrile facilitates dissolution of adsorbed water from the silica shells and disperses it into the bulk acetonitrile/cyanoacrylate solution. This initiated the poly-condensation much more rapidly than when the water primarily remains adsorbed on the surface of the silica shells in DCM solvent.

The thickness of the PMCA/micro-shells film can be controlled by varying the concentration of the particles in glue and the number of dip coating repetition. To test the effect of the number of coating cycles, 20 mg/ml particles in methyl-2-cyanoacrylate were coated onto glass slides with different numbers of repetitions. The film thickness on glass slides are 15±3 um, 31±5 um, 59±11 um and 98±13 um (5 samples each) by dip coating the slides 1, 2, 3 and 4 times, respectively. Multiple coatings were needed to form a uniform PMCA/micro-shells film on the needles. A film with a thickness of 18±5 um was obtained by dip coating surgical needles 8 times each in micro-shells/glue/DCM mixture; this was replicated in 10 needles. The data is consistent with the surface tension of the round shape of the needle and the surface energy of metal requiring more coatings for the needles. High particle concentration produces thicker films after curing as compared to low particle concentrations. When 10 mg/ml particles in methyl-2-cyanoacrylate were coated on needles, a film with a thickness of 8±3 um was obtained by dip coating 10 needles 8 times each in silica shells/glue/DCM mixture.

Figure 12:
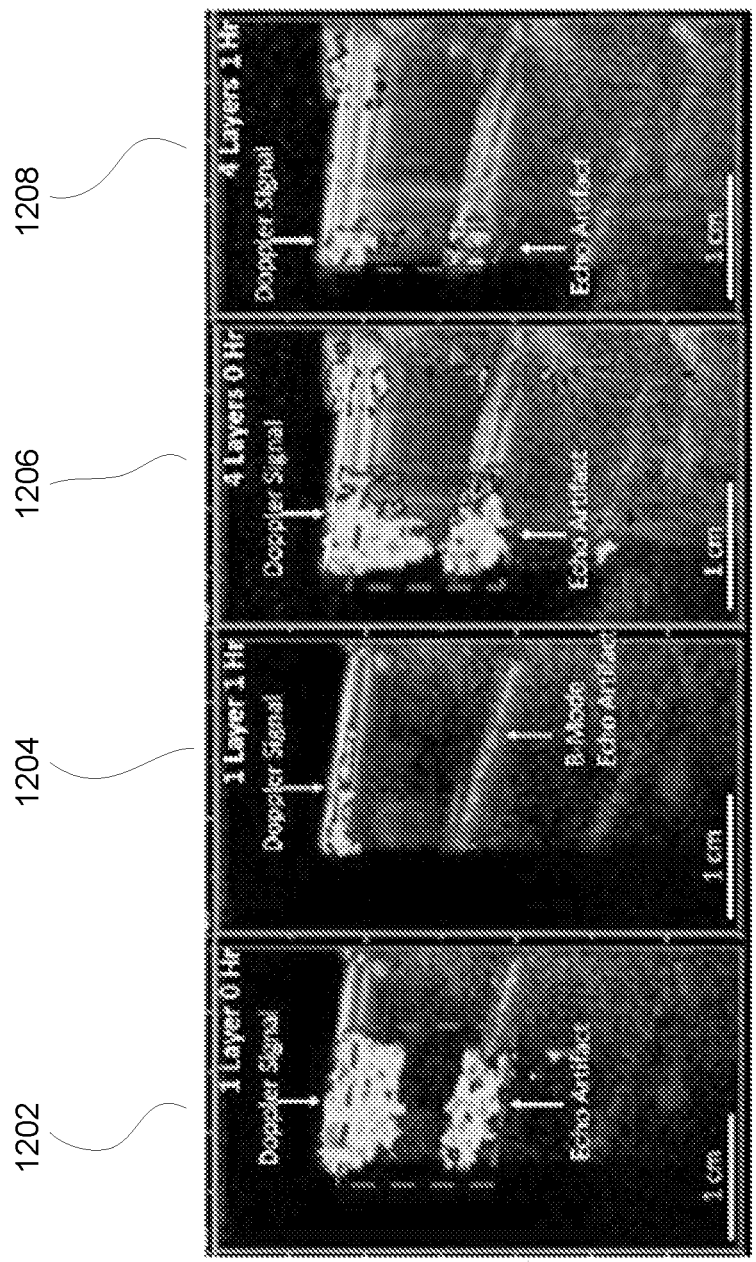
FIG. 12 shows another exemplary color Doppler images of silica PMCA/micro-shells macro-phase separated films on a glass slide.

Exemplary In Vitro Ultrasound Performance and Macro-Phase Separation of PMCA/Micro-Shells Films FIG. 12 displays the color Doppler signals from PMCA/micro-shells films on glass slides. Strong color Doppler signals (e.g., in 1202 and 1206) were observed from films produced by the dip coating method with DCM as solvent. The broad upper colored image and the secondary image below the signal around the position of glass slides are a known acoustic echo, which is an artifact that is characteristic of very strong ultrasound color Doppler signals. For such strong ultrasound imaging, it is likely that the ultrasound pulses release trapped air from the surface microshells to create microbubbles and the strong broadband signal. As the air is released over time, indicated by 1204 and 1208, the image intensity weakens as the surface layer of micro-shells release most of the trapped gas.

In some embodiments, air is used as the contrast agent within the hollow space of silica shells. For micro-shells in aqueous solution, normally perfluorocarbon gas is necessary for ultrasound activity to prevent gas diffusion/dissolution from the porous micro-shells and consequent filling of the micro-shells with water; however, with the polymer coating, simple air filling can be employed since the polymer likely seals the micro-shell pores. When air-filled 2 μm boron-doped silica micro-shells were suspended in deionized water without cyanoacrylate coating, no color Doppler signals were observed, indicating that water enters the micro-shells and dissolves the air. After mixing with methyl-2-cyanoacrylate glue, the macro-phase separated PMCA/micro-shells film can be imaged, and the film gave strong color Doppler signals that persisted for several hours when exposed to continuous insonation (1204 and 1208). In another test, PMCA/micro-shells film coated surgical needles were dipped in water bath with a temperature of 37°

C. for 4 months and strong color Doppler signals were obtained. This shows that air was sealed within the shell by the rapid curing of glue on the hydrated silica surface and possibly even in the pores of the silica shells.

Figure 13B:
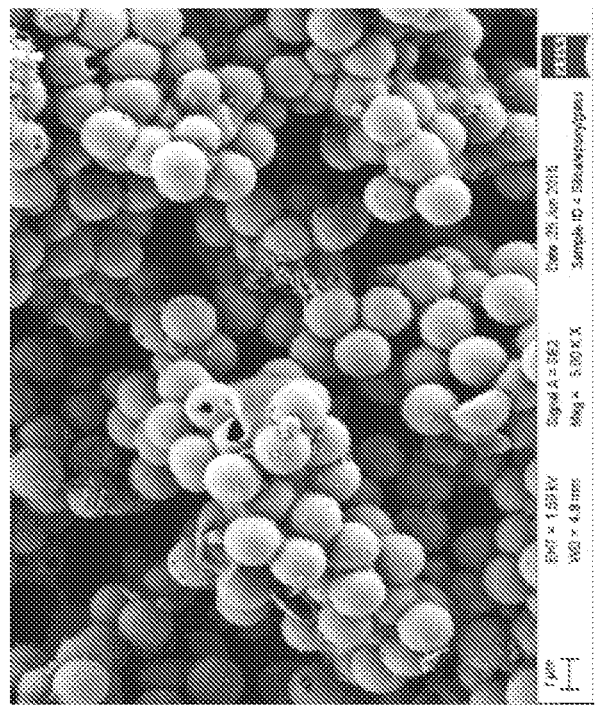
FIG. 13(b) shows an exemplary TEM image of macro-phase separated micro-shells films coated on 2 cm stainless steel wires with scale bars being 2 μm.
Figure 13A:
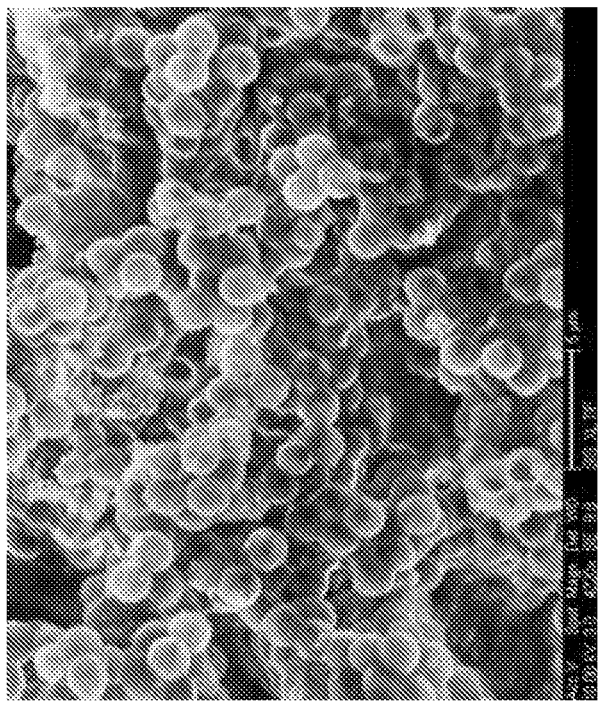
FIG. 13(a) shows an exemplary SEM image of macro-phase separated micro-shells film coated on 2 cm stainless steel wires with scale bars being 5 μm.

FIG. 13(a) and FIG. 13(b) are exemplary SEM and STEM images of the surfaces of silica PMCA/micro-shells film on glass slides. In some embodiments, the film was coated on 2 cm stainless steel wires. The cyanoacrylate coated shells formed clusters of cross-linked shells with a thin, loose, porous 3D network of polymer film binding the shells. The thin polymer film on the surface and in the pores of the micro-shells may block the pores in the calcined silica gel wall and seals air within the hollow space, thereby providing good ultrasound contrast performance. The contact angle of the PMCA/micro-shells film on the glass slide was measured to be 130°, which is consistent with the micro-shells being covered with a thin hydrophobic polymeric film.

In some embodiments, perfluorocarbon loaded silica nano- and micro-shells can give strong color Doppler signals when suspended in water or animal tissues. Unlike soft microbubble based ultrasound contrast agents, silica shells are rigid and non-elastic. The micro-shells exhibit a large acoustic impedance mismatch between the surrounding fluid environments. When silica shells are subjected to an ultrasound wave, the shells fracture and release entrapped PFP gas; the released gas is able to expand and contract to generate a non-linear ultrasound signal. The air in the hollow shell works as the ultrasound contrast agent in the cyanoacrylate films. When the PMCA/micro-shells film is subjected to continuous ultrasound waves, the air in the hollow space escapes from the fractured silica shells near the surface so the color Doppler signal attenuates over time.

Figure 14:
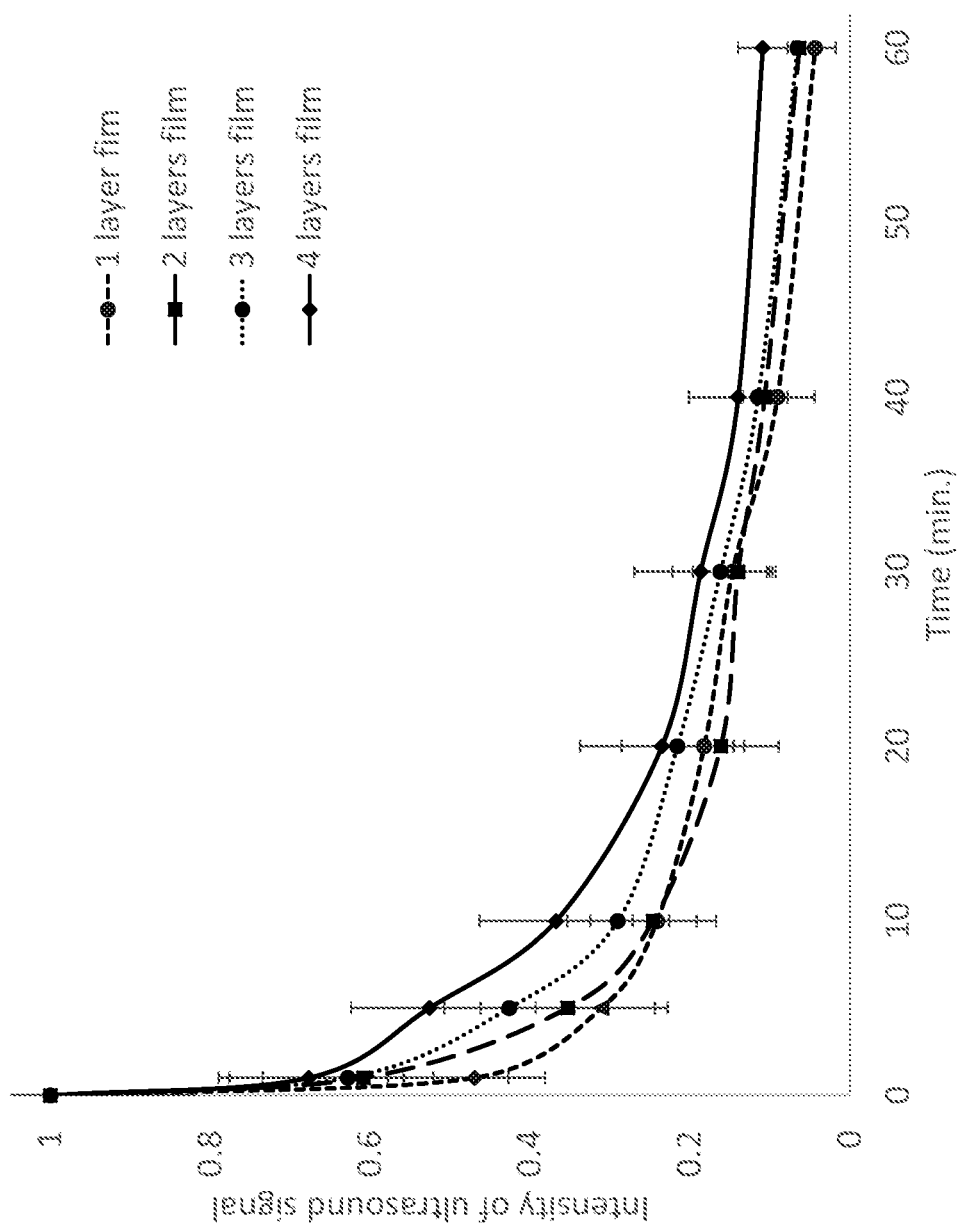
FIG. 14 shows an exemplary attenuation rates of color Doppler signals of films with different thickness.

The relationship between the attenuation rate and the thickness of the PMCA/micro-shells films on glass slides was studied. FIG. 14 shows the attenuation rates of color Doppler signals of films with different thickness. Note that the intensities were normalized to 1 at time zero. After subjecting the film to continuous ultrasound for one hour, the area of color Doppler signal of all films with different thickness decayed to less than 11% of the initial intensity. With increasing film thickness, the ultrasound signals attenuated more slowly, but their effect is small. This indicates that with more dip coating repetition times, more silica micro-shells were deposited on the surface of film, but saturation is quickly reached. It also indicates that only a small fraction of the shells are releasing gas at any instant in time.

Figure 15:
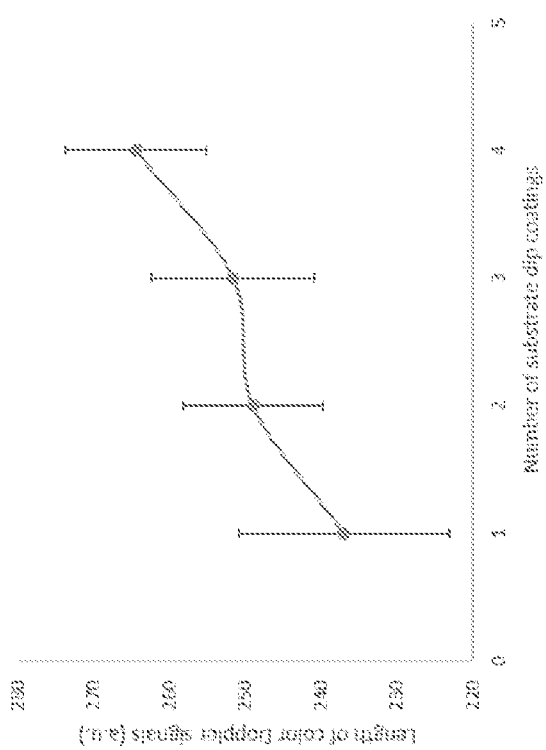
FIG. 15 shows an exemplary comparison of the intensity of initial ultrasound signals of films with different thickness.

FIG. 15 compares the intensity of initial ultrasound signals of films with different thickness. The vertical image length of the color Doppler signal on the screen was used it to represent the intensity of the ultrasound signals. More dip coating repetitions slightly increased the image size. This is consistent with increased dip coating repetitions increasing the density of micro-shells in the surface layer to produce stronger initials signals and slower attenuation but saturation is quickly reached.

FIG. 16(a) shows an SEM image of an exemplary cross section of the PMCA/micro-shells film coated on the glass slide with DCM as the solvent. In this particular example, the film was exfoliated from the slide for imaging. The arrow 1602 indicates the boundary between the domain of the polymer and the domain of polymer/micro-shells. The flat plate is the polymer film surface which was proximal to the glass slide and no silica micro-shells were observed on this surface. In the cross section, a region of pure polymer matrix and a region composed of polymer and 2 μm shells were clearly observed (separated by red dash line). On the surface of the film there is another loose layer consisting of mainly 2 μm shells (as shown in FIG. 13(a)). Three domains present in the film indicate that a macro-phase separation occurred during solvent evaporation and polymerization of the cyanoacrylate/micro-shell composite. When ethyl acetate is employed as solvent, phase separation was also observed in the film and an ultrasound signal was obtained from the film. If DCM is replaced with acetonitrile as solvent for the coating, no obvious ultrasound signal was imaged from the film on the glass slide. FIG. 16(b) shows an SEM image of another exemplary cross section of the film cured with acetonitrile solvent on a surgical needle. Arrow 1604 indicates the cross section of the film. Arrow 1606 indicates the surface of the metal needle. No obvious phase separation was found in the cross section. FIG. 16(c) is the SEM image of an exemplary front surface of the film on the surgical needle with acetonitrile as solvent. Only a few silica particles were evident and no appreciable ultrasound signal was obtained from the film. FIG. 16(d) is the SEM image of an exemplary cross section of the acetonitrile based film on a surgical needle cured in glove box. Arrow 1608 indicates the boundary between the domain of polymer and the domain of polymer/micro-shells. Arrow 1610 indicates the metal needle surface. The scale bars in all figures are 10 μm.

Phase separation in polymer-nanoparticles composites has been studied as well. Enthalpic and entropic interactions between polymer chains and nanoparticles contribute to phase separation. When polymer chains grow across solid silica particles, they become constrained, which results in loss of conformational entropy. Larger particles are easier to expel from polymers than smaller particles. In some embodiments, phase separation depends on the speed of polymerization of the cyanoacrylate monomer solution, which shows that macro-phase separation may be altered by kinetic control of the curing process. The curing of cyanoacrylate glue is a typical anionic polymerization and high polarity solvents facilitate more rapid polymerization by producing more free ions, as well as aiding the dissolution of adsorbed water (a polymerization aid that reacts with the cyanoacrylate acid inhibitor). Acetonitrile has a high polarity (polarity index is 5.8 compared to that of DCM at 3.1) and the curing of cyanoacrylate is faster in acetonitrile solvent than in DCM and ethyl acetate. Hydrophilic acetonitrile may carry cyanoacrylate monomer through the hydrophilic nano-porous walls of micro-shells, but the hydrophobicity and viscosity of the DCM/glue mixture makes the displacement of air from silica micro-shells difficult. In acetonitrile, when the length of the polymerized chains increases rapidly inside and outside the micro-shells, the micro-shells become filled with polymer and trapped within the polymer matrix. After evaporation of solvent, the thick solid polymer matrix makes the micro-shells non-activable to ultrasound waves.

With DCM or ethyl acetate as solvent, the curing is slower than with acetonitrile; therefore, micro-shells are driven out of the matrix of short chains of polymer during curing to obtain a thermodynamically favored macro-phase separated composite. With DCM as a solvent, less polar DCM might not be able to efficiently carry monomers through the polar nano-pores of the micro-shells. Slow curing also keeps the glue-solvent mixture with a low viscosity which allows the micro-shells phase segregate. At the same time, there is a thin polymer film coating and binding the air-filled surface silica micro-shells. This coating is too thin to block the ultrasound wave but sufficiently thick to seal the pores of silica shell thereby allowing the micro-shells to retain trapped air in the hollow space as ultrasound contrast agent for long time periods.

While the films with phase separated micro-shells surface layers gave strong color Doppler signals, no ultrasound signals were imaged when the film was a uniform single phase and the shells were embedded deeper in the polymer matrix. Few 2 um micro-shells are observed in the cross section of the single phase film with acetonitrile as solvent (FIG. 16(b)). The poly-cyanoacrylate filled in the hollows space of micro-shells and air was expelled. The film with two partially separated domains (ethyl acetate solvent) also gave color Doppler signals but not as strong as the film (DCM solvent) with the dense micro-shell surface layer and the ultrasound signals attenuated quickly. The data is consistent with only the micro-shells near the surface of the film being activated by ultrasound waves.

The relationship between the phase separation and the speed of polymerization was further probed by coating PMCA/micro-shells films on surgical needles in a glove box filled with nitrogen with acetonitrile as polymerization solvent. Without the presence of atmospheric moisture, cyanoacrylate curing in acetonitrile is significantly slower, allowing enough time for macro-phase separation during the slower polymer chain elongation process. FIG. 16(d) shows the obvious macro-phase separation in the film, and color Doppler signals were readily obtained from this film. In the glove box, trace moisture to initiate polymerization inhibitor can only come from the water adsorbed on the silica micro-shells, and the polymerization of cyanoacrylate was much slower than air curing the dip coated films. The extremely slow curing may allow the micro-shells time to phase segregate. When the micro-shells are close to the surface of film air may diffuse into the hollow space while cyanoacrylate monomer and oligomer partly carried out of the micro-shells with the evaporating solvent. A macro-phase separation was thereby obtained by the slower polymerization process. The film is also ultrasound active, but not as active as those cast using DCM solvent.

Figures 17A, 17B:
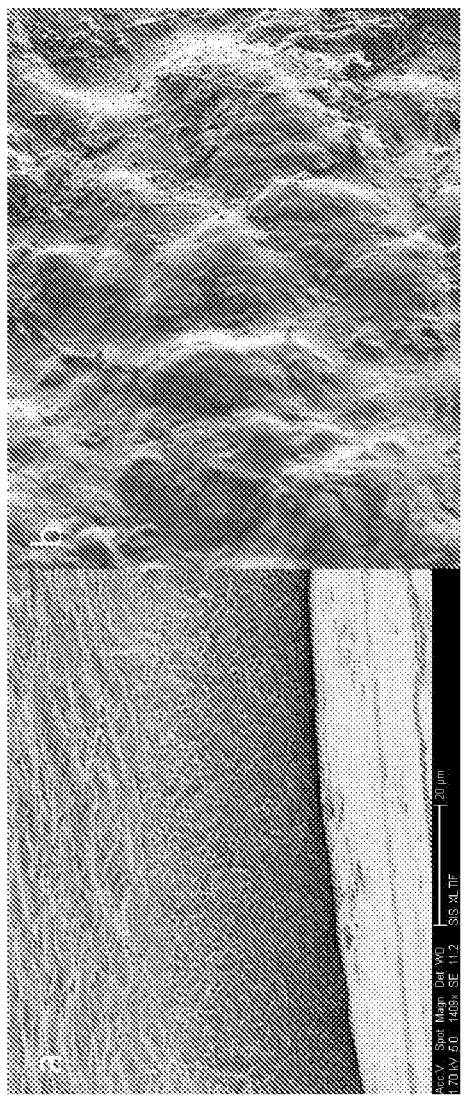
FIG. 17(a) shows an exemplary SEM image of the cross section of 10 mg/ml micro-shells/cyanoacrylate glue film coated on a 20 gauge hypodermic needle with a uniform microshells-glue phase in the cross section.
FIG. 17(b) shows an exemplary STEM image of the surface of 10 mg/ml micro-shells/cyanoacrylate glue film coated on a 20 gauge hypodermic needle with no loose, surface layer of crosslinked micro-shells observed.

It also was found that the phase separation was dependent on the concentration of micro-shells in cyanoacrylate glue. When 10 mg/ml particles in methyl-2-cyanoacrylate/DCM were dip coated onto needles with four repetitions no obvious polymer domain was observed. FIG. 17(a) shows an SEM image of an exemplary cross section of 10 mg/ml micro-shells/cyanoacrylate glue film coated on a 20 gauge hypodermic needle with a uniform microshells-glue phase in the cross section. FIG. 17(b) shows an STEM image of an exemplary surface of 10 mg/ml micro-shells/cyanoacrylate glue film coated on a 20 gauge hypodermic needle with no loose, surface layer of crosslinked micro-shells observed. In SEM and STEM images the cross section of the film is analogous to the micro-shells/poly-cyanoacrylate layer in the phase separated film but there is no loose micro-shells surface layer. Strong color Doppler ultrasound signals were obtained from the film but the signals attenuated rapidly. This shows that the macro-phase separation did not occur because the poly-cyanoacrylate chains were less constrained in solutions comprising a lower concentration of micro-shells than in solutions comprising the high concentration of micro-shells. It should be noted that solvent plays a role, since the non-phase segregated films with rapidly attenuating color Doppler properties were obtained from DCM solvent. With acetonitrile solvent, phase segregated films were never observed and no weak color Doppler signal can be observed. The inactivity of films prepared from acetonitrile can be attributed to loss of gas and filling of the micro-shells with polymer. Such films are optically clear, in contrast to the white opaque films comprising gas filled shells.

To test the PMCA/micro-shells film as a multi-purpose marker for surgical tools, coated needles were hidden in animal organs and located with a clinical ultrasound machine. FIG. 18(a) displays the color Doppler image of a coated 18 mm (⅜ curved) needle in pork liver obtained with a 15L8 transducer with a ultrasound center frequency of 7 MHz. The needle is co-planar parallel with the plane of ultrasound waves. Strong color Doppler signals 1802 were observed, and the needle was very easily identified from the background. From the scale bar on the side of the image, the depth of the needle in pork liver can be confirmed as about 0.5 centimeter. The depth of the signal is larger than the diameter of the needle because of the strong acoustic echo. FIG. 18(b) displays the ultrasound image of the same needle, but the needle is perpendicular to the plane of ultrasound waves. The bright spot shows only the cross section of the needle, and the dark tail extending down from the needle is the B-mode acoustic echo of the needle due to the strong signal. The color Doppler signal 1804 of needles did not significantly attenuate after remaining in the liver tissue for 6 hours (without continuous imaging), which indicates that tissue or blood has little effect on degrading the film's image intensity.

Figure 18C:
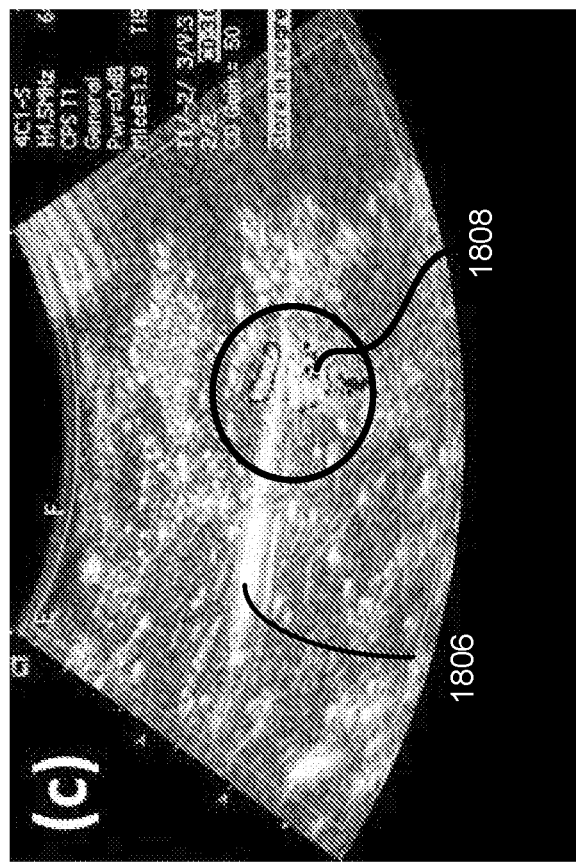
FIG. 18(c) shows an exemplary in-plane view of macro-phase separated PMCA/micro-shells film coated 18 mm needle in pork liver using a 4C1 transducer and an ultrasound frequency of 3 MHz.
Figure 18B:
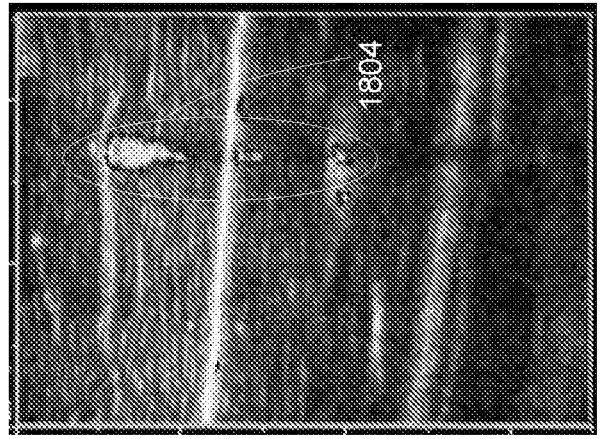
FIG. 18(b) shows an exemplary cross sectional view of macro-phase separated PMCA/micro-shells film coated 18 mm needle in pork liver with 15L8 transducer and an ultrasound frequency of 7 MHz.
Figure 18A:
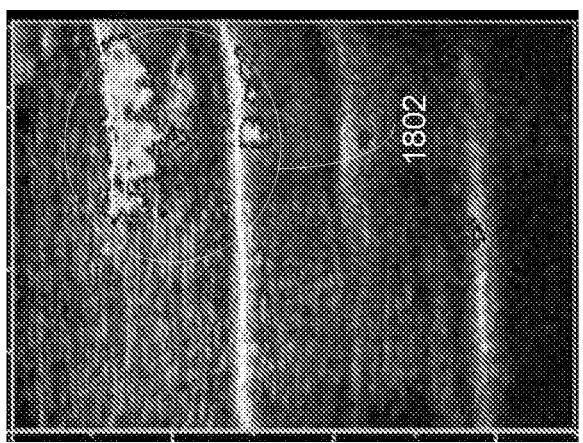
FIG. 18(a) shows an exemplary in-plane view of macro-phase separated PMCA/micro-shells film coated 18 mm needle in pork liver with 15L8 transducer and an ultrasound frequency of 7 MHz.

FIG. 18(c) displays the ultrasound image of a coated 18 mm (⅜ curved) needle in a plastic box filled with chicken livers to mimic an organ cavity environment. The image was obtained with a 4C1 transducer with a center frequency of 3 MHz so that a deeper image can be obtained. The needle was easily identified by its strong color Doppler signals 1808. The white stripe 1806 between the signal of the needle and its shadow is the acoustic echo from the bottom of the box. The needle was about 5 centimeters from the top of the box comprising densely packed livers. The low frequency transducer can penetrate deeper in animal tissues than the high frequency transducer, although the latter displays better spatial resolution.

Exemplary In Vivo Ultrasound Testing

Figure 19A:
FIG. 19(a) shows an exemplary color Doppler image of macro-phase separated PMCA/micro-shells film coated surgical needles in live rabbit.
Figure 19B:
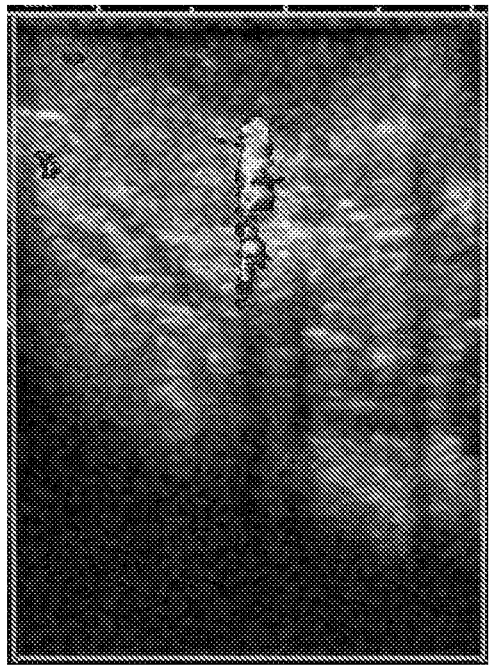
FIG. 19(b) shows another exemplary color Doppler image of macro-phase separated PMCA/micro-shells film coated surgical needles in live rabbit.
Figure 19C:
FIG. 19(c) shows an exemplary color Doppler image of macro-phase separated PMCA/micro-shells film coated umbilical tape in live rabbit.
Figure 19D:
FIG. 19(d) shows an exemplary color Doppler image of macro-phase separated PMCA/micro-shells film coated surgical clips in live rabbit.
Figures 20A, 20B, 20C:
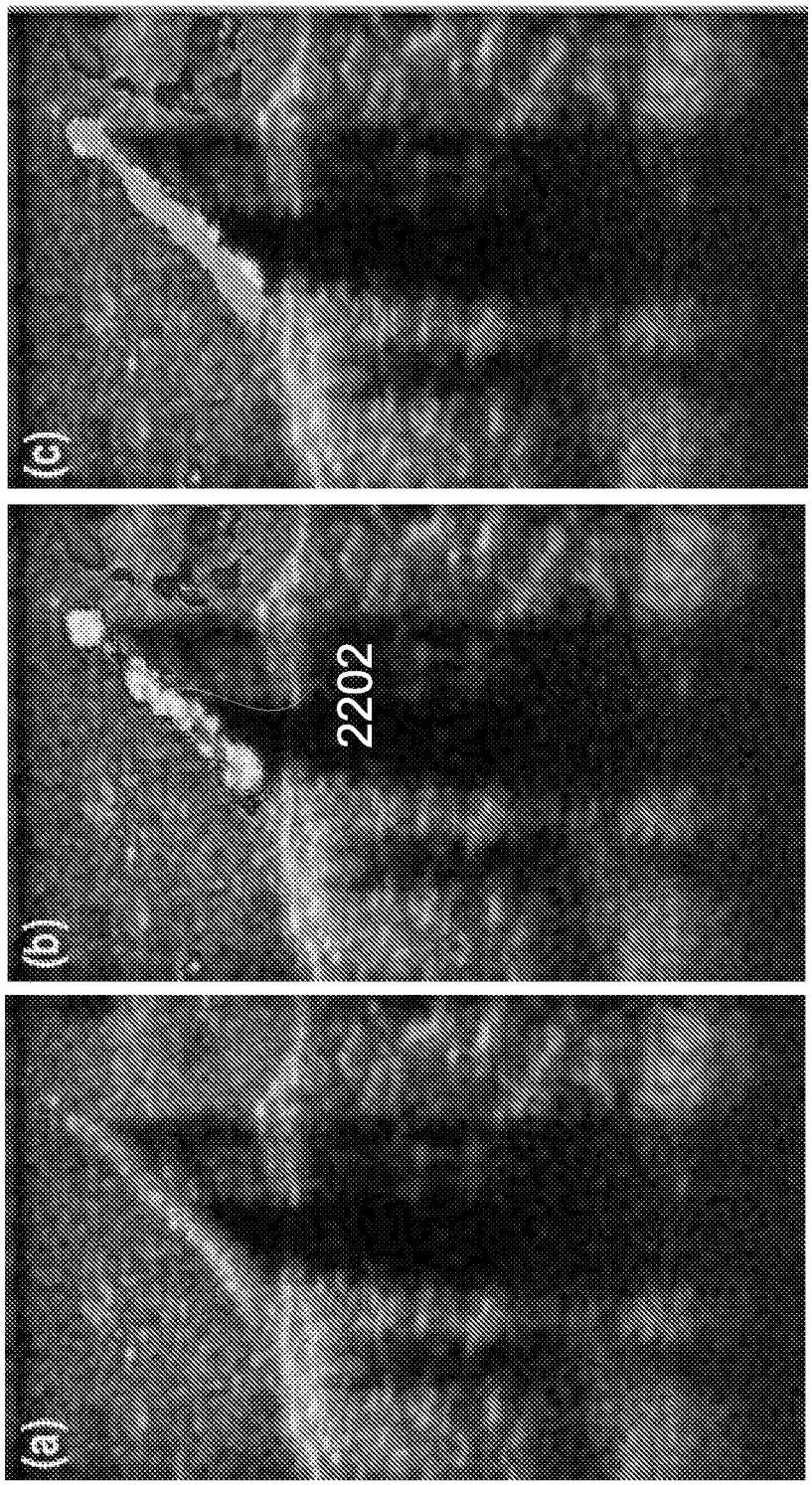
FIG. 20(a) shows an exemplary post-process image of macro-phase separated PMCA/micro-shells film coated 790 nm diameter stainless steel wire with 15L8 transducer showing strong B-mode signal with persistently high spatial.
FIG. 20(b) shows an exemplary post-process image of macro-phase separated PMCA/micro-shells film coated 790 nm diameter stainless steel wire with 15L8 transducer showing temporal heterogeneity in the simultaneous color Doppler image.
FIG. 20(c) shows an exemplary post-process image of macro-phase separated PMCA/micro-shells film coated 790 nm diameter stainless steel wire with 15L8 transducer showing green overlay of a micro-shell signal (MSS).

FIG. 19(a)-(d) show the color Doppler images of PMCA/micro-shells coated surgical needle, umbilical tape, and a surgical clip in the abdomen of a live rabbit. The images were obtained with a 15L8 Transducer and a ULTRASOUND center frequency of 7 MHz. These surgical tools were covered by organs such as intestines, liver lobes, bladder or spleen. FIG. 20(a) shows an exemplary post-process image of macro-phase separated PMCA/micro-shells film coated 790 nm diameter stainless steel wire with 15L8 transducer showing strong B-mode signal with persistently high spatial. FIG. 20(b) shows temporal heterogeneity in the simultaneous color Doppler image. FIG. 20(c) shows the overlay of a micro-shell signal (MSS). As shown in FIG. 20(a)-(c), the coated surgical items exhibited strong color Doppler signals 2002 and can be easily located. PMCA/micro-shells coated surgical needles gave strong color Doppler signals when the needle is co-planar parallel with the plane of ultrasound waves (FIG. 19(a)). Since the needles have very small surface areas and the lost needles can be at any angle to the transducer, aligning the needles and the plane of ultrasound waves to ensure parallel geometry can be challenging with only a 2D ultrasound transducer. When the tiny needle is perpendicular to the plane of ultrasound waves it has the smallest surface area exposed to the insonation. FIG. 8b shows the color Doppler signals of a needle which is perpendicular to the ultrasound waves. The signals are strong and allow for the needle to be easily located within the tissue. The images of needles parallel and perpendicular to the plane of ultrasound waves are similar with the images obtained during the in vitro test, which shows that the living animal tissues did not have prevent ultrasound detection. FIG. 19(c) and FIG. 19(d) are images of a coated, cotton umbilical tape and a standard surgical clip in the abdomen of rabbit. The color Doppler signals are very strong due to the relatively larger surface area and increased amount of silica shells that can be activated by the ultrasound waves when compared to the much smaller surgical needles. Alignment of the US transducer is much easier for imaging the items larger than surgical needles.

To improve identification of small items, such as surgical needles, an algorithm was used for image processing to highlight the location of small items for the viewer. The results of the micro-shells signal detection algorithm described in the experimental section are shown in FIG. 20(c) where the detected processed micro-shell signal (MSS) is shown as a green overlay. This is an in situ technology to differentiate the film's signals from background noise and possible interfering signals from vessels or other organs and make the searching and locating of medical devices fast and accurate, which is important for minimizing training costs and the use of operating room time. The data of Doppler and MSS signals and signal to noise rations (SNRs) is in supplementary information. In vitro and in vivo tests showed PMCA/micro-shells film coated needles, umbilical tapes and surgical clips can be easily located in live animal tissues and organs.

This technology demonstrates applications of locating and monitoring surgical tools that are deep within a tissue cavity with ultrasound imaging. Similar coating methods can be used to coat this ultrasound activate film on other metal, plastic, glass, and other surgical items that benefit from more accurate placement within the body using ultrasound imaging. The image intensity can be controlled by changing the concentration of nano-shells to provide optimum tip image intensity for a particular depth application.

One advantageous aspect is that this technology provides a simple and low cost method to improve the visibility and placement of surgical, therapeutic, diagnostic, and other medical devices that use ultrasound image guidance. Potential application of this technology include, but are not limited to, (1) coating needles for biopsies and therapeutic applications, (2) placement of clips for marking tumors, (3) ultrasound guided needle delivery of local anesthetics, drugs, and other therapies, (4) catheters for central lines, drainage, and other applications, (5) selective marking of needle and catheter and other tool tips for improved imaging by color Doppler, (6) coating plastic catheters and other objects for better visualization deep within the body, (7) insertion of central lines and IV lines in arteries or veins, (8) retained surgical items detecting, (9) biopsy marker such as a clip for cancer diagnosis, (10) ultrasound activated drug delivery, and (11) other medical implants monitoring.

Figure 22:
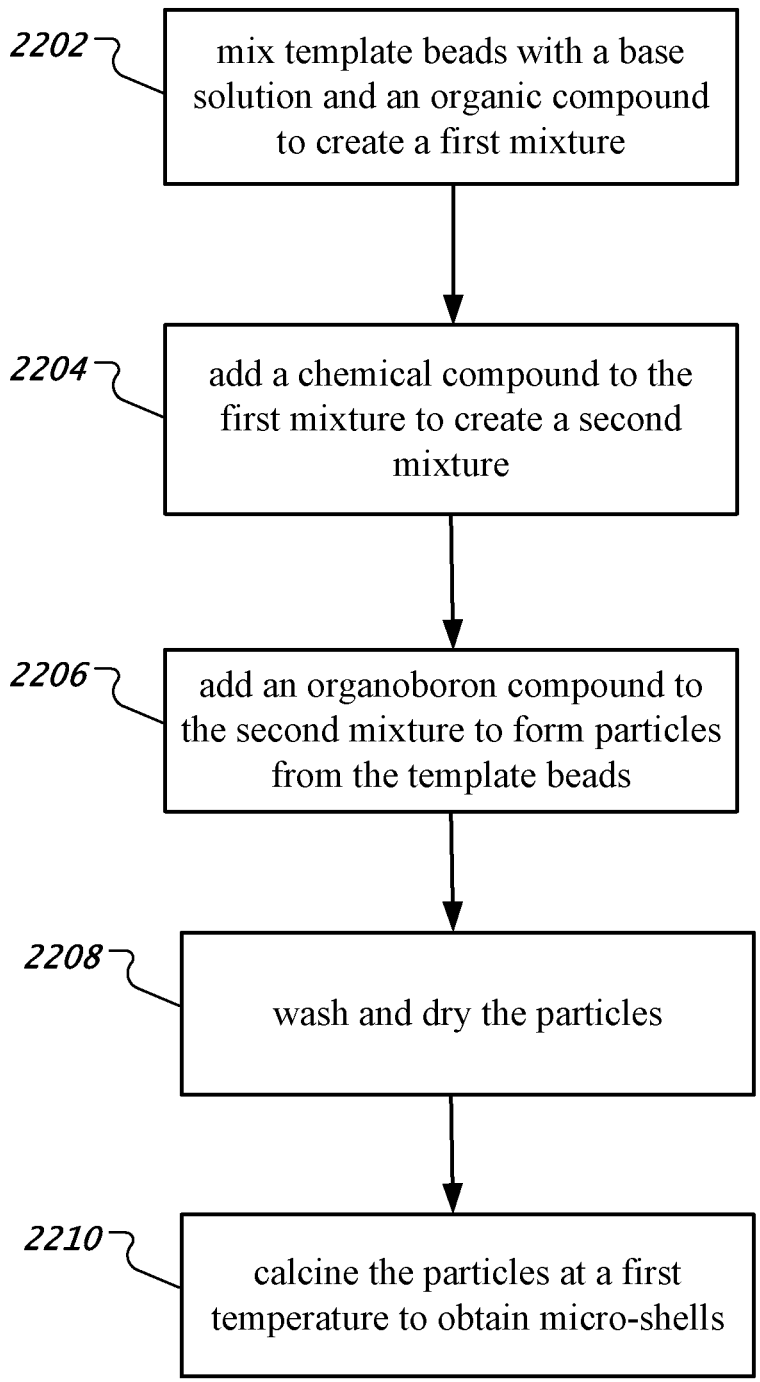
FIG. 22 shows an exemplary flowchart for the process of synthesizing micro-shells.
Figure 23:
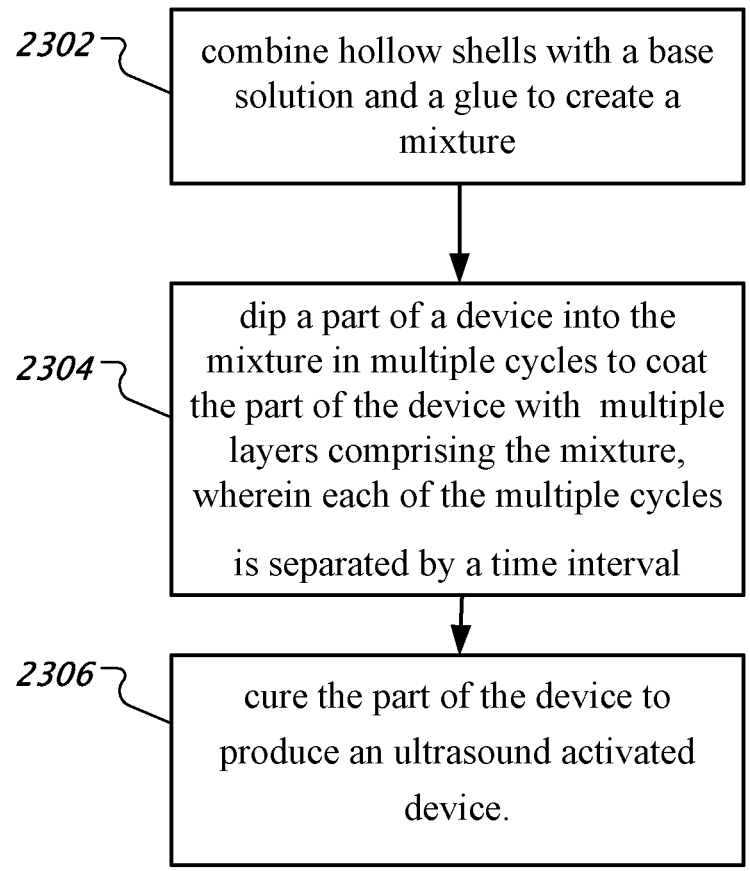
FIG. 23 shows an exemplary flowchart of the process of synthesizing an ultrasound activated marker.

FIG. 22 shows a flowchart of the synthesizing process for micro-shells. The process comprises mixing template beads with a base solution and an organic compound to create a first mixture, wherein the base solution reacts with the organic compound 2202; adding a chemical compound to the first mixture to create a second mixture 2204; adding an organoboron compound to the second mixture to form particles from the template beads 2206; washing and drying the particles 2208; and calcining the particles at a first temperature to obtain micro-shells 2210. In some embodiments, the template beads comprise polystyrene beads. Diameters of the polystyrene beads can range from 0.2 µm to 6 µm. In some embodiments, the base solution is 95% ethanol, the organic compound is 0.2% diethylenetriamine (DETA), the chemical compound is Tetramethylorthosilicate (TMOS), and the organoboron compound is trimethyl borate (TMB).

FIG. 22 shows a flowchart of the synthesizing process for the ultrasound activated marker. The process comprises combining hollow shells with a base solution and a glue to create a mixture 2302; dipping the substrate into the mixture in multiple cycles to coat the substrate with multiple layers comprising the mixture 2304, wherein each of the multiple cycles is separated by a time interval; and curing the substrate with multiple layers comprising the mixture at room temperature to produce the ultrasound activated marker 2306. In some embodiments, the base solution comprises dichloromethane (DCM) and the glue comprises methyl-2-cyanoacrylate. In some embodiments, the substrate includes a glass slide, a surgical needle, a surgical clip, or an umbilical tape. The time interval can be 10 minutes.

The disclosed and other embodiments and the functional operations described in this document, such as measurements, data collection, and data processing, can be implemented in digital electronic circuitry, or in computer software, firmware, or hardware, including the structures disclosed in this document and their structural equivalents, or in combinations of one or more of them. The relevant operations for the disclosed and other embodiments can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this document can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. An ultrasound activated marker, comprising:
a layer of polymeric matrix; and
hollow shells at least partially embedded in the layer of polymeric matrix, and positioned close to a top surface of the layer of polymeric matrix, wherein each of the hollow shells is configured to retain air in a hollow core and provide an ultrasound contrast agent for ultrasound imaging, and
wherein the hollow shells are silica hollow shells that are provided from polystyrene beads with an organic compound that includes diethylenetriamine (DETA) in a base solution including ethanol, and
wherein surfaces of the polystyrene beads are modified by the DETA that is adsorbed onto the surfaces of the polystyrene beads.

2. The marker of claim 1, wherein the layer of polymeric matrix comprises polymethyl-2-cyanoacrylate (PMCA).

3. The marker of claim 1, wherein the hollow shells are biocompatible.

4. The marker of claim 1, wherein the hollow shells are silica hollow shells having a diameter ranging from 0.1 µm to 6 µm.

5. The ultrasound activated marker of claim 1, wherein the hollow shells are doped with boron to increase mechanical strength of the hollow shells.

6. The ultrasound activated marker of claim 1, wherein the layer of polymeric matrix is configured to seal pores of the hollow shells and keep the air within the hollow cores.

7. The ultrasound activated marker of claim 1, wherein the polystyrene beads have a diameter ranging from 0.2 µm to 6 µm.

8. The ultrasound activated marker of claim 1, wherein the polystyrene beads and the organic compound are mixed with the base solution that includes ethanol.

9. The ultrasound activated marker of claim 1, wherein the top surface of the layer of polymeric matrix is hydrophilic.

10. The ultrasound activated marker of claim 1, wherein the hollow shells include epoxy adhesive, cyanoacrylate glue, hydrogels or organogels.

11. The ultrasound activated marker of claim 1, wherein the layer of the polymeric matrix crosslinks the hollow shells.

12. An ultrasound activated marker, comprising:
a volume of polymeric matrix; and
hollow shells dispersed in the volume of polymeric matrix, wherein each of the hollow shells is configured to retain air in a hollow core and provide an ultrasound contrast agent for ultrasound imaging, and
wherein the hollow shells are silica hollow shells that are provided from polystyrene beads with an organic compound that includes diethylenetriamine (DETA) in a base solution including ethanol, and
wherein surfaces of the polystyrene beads are modified by the DETA that is adsorbed onto the surfaces of the polystyrene beads.

13. The marker of claim 12, wherein the volume of polymeric matrix comprises 1% agarose hydrogel.

14. The marker of claim 12, wherein the hollow shells are octyl modified silica hollow shells.

15. The ultrasound activated marker of claim 12, wherein the hollow shells are doped with boron to increase mechanical strength of the hollow shells.

16. The ultrasound activated marker of claim 12, wherein the volume of polymeric matrix is configured to seal pores of the hollow shells and keep the air within the hollow cores.

17. The ultrasound activated marker of claim 12, wherein the polystyrene beads have a diameter ranging from 0.2 µm to 6 µm.

18. The ultrasound activated marker of claim 12, wherein the polystyrene beads and the organic compound are mixed with the base solution that includes ethanol.

19. The ultrasound activated marker of claim 12, wherein a top surface of the volume of polymeric matrix is hydrophilic.

20. The ultrasound activated marker of claim 12, wherein the hollow shells are silica hollow shells having a diameter ranging from 0.1 µm to 6 µm.

\* \* \* \* \*

UNITED STATES PATENT AND TRADEMARK OFFICE
CERTIFICATE OF CORRECTION

PATENT NO. : 11,813,123 B2
APPLICATION NO. : 16/329669
DATED : November 14, 2023
INVENTOR(S) : Jian Yang et al.

It is certified that error appears in the above-identified patent and that said Letters Patent is hereby corrected as shown below:

On the Title Page

On Page 2, in Item (57), under "ABSTRACT", in Column 1, Line 4, delete "segregated in" and insert --segregated--, therefor.
On Page 2, in Item (56), under "OTHER PUBLICATIONS", in Column 2, Line 16, delete "Reporton" and insert --Report on--, therefor.

In the Specification

In Column 2, Line 30, delete "image" and insert --image of--, therefor.
In Column 3, Line 2, delete "um" and insert --µm--, therefor.
In Column 3, Line 3, delete "um." and insert --µm.--, therefor.
In Column 3, Line 5, delete "um" and insert --µm--, therefor.
In Column 3, Line 6, delete "um." and insert --µm.--, therefor.
In Column 9, Line 53, delete "(lacotite" and insert --(loctite--, therefor.
In Column 9, Line 62, delete "2-caynoacrylate/2 um" and insert --2-cyanoacrylate/2 um--, therefor.
In Column 15, Lines 19-20, delete "trimethy" and insert --trimethyl--, therefor.
In Column 15, Line 30, delete "430" and insert --430™--, therefor.
In Column 17, Line 50, delete "used it" and insert --used--, therefor.
In Column 22, Line 36, delete "them." and insert --of them.--, therefor.
In Column 23, Lines 25-26, delete "CD ROM" and insert --CD-ROM--, therefor.

Signed and Sealed this
Ninth Day of April, 2024

Katherine Kelly Vidal
*Director of the United States Patent and Trademark Office*